US008975019B2

(12) United States Patent
Zamore et al.

(10) Patent No.: US 8,975,019 B2
(45) Date of Patent: Mar. 10, 2015

(54) DEDUCING EXON CONNECTIVITY BY RNA-TEMPLATED DNA LIGATION/SEQUENCING

(75) Inventors: Phillip D. Zamore, Northborough, MA (US); Melissa J. Moore, Chestnut Hill, MA (US); Christian Roy, Shrewsbury, MA (US)

(73) Assignee: University Of Massachusetts, Boston, MA (US)

( * ) Notice: Subject to any disclaimer, the term of this patent is extended or adjusted under 35 U.S.C. 154(b) by 353 days.

(21) Appl. No.: 12/906,678

(22) Filed: Oct. 18, 2010

(65) Prior Publication Data

US 2011/0092375 A1    Apr. 21, 2011

Related U.S. Application Data

(60) Provisional application No. 61/252,868, filed on Oct. 19, 2009.

(51) Int. Cl.
*C12Q 1/68* (2006.01)
*C07H 21/00* (2006.01)
*C07H 21/02* (2006.01)
*C07H 21/04* (2006.01)
*C12N 15/10* (2006.01)
*C12N 15/66* (2006.01)

(52) U.S. Cl.
CPC ........ *C12N 15/1031* (2013.01); *C12N 15/1096* (2013.01); *C12Q 1/6806* (2013.01); *C12Q 1/6869* (2013.01); *C12N 15/66* (2013.01)
USPC .......... 435/6.1; 536/22.1; 536/23.1; 536/24.3

(58) Field of Classification Search
CPC ....... C12Q 1/68; C12Q 1/6844; C12Q 1/6862
USPC .......................... 435/6.1; 536/22.1, 23.1, 24.3
See application file for complete search history.

(56) References Cited

U.S. PATENT DOCUMENTS

| | | | | |
|---|---|---|---|---|
| 4,683,195 | A | 7/1987 | Mullis et al. | 435/6.11 |
| 4,683,202 | A | 7/1987 | Mullis | 435/91.2 |
| 5,538,848 | A | 7/1996 | Livak et al. | 435/6.16 |
| 5,639,606 | A | 6/1997 | Willey | 435/6.12 |
| 5,643,765 | A | 7/1997 | Willey | 435/91.2 |
| 5,750,341 | A | 5/1998 | Macevicz | 435/6.19 |
| 5,846,717 | A | 12/1998 | Brow et al. | 435/6.18 |
| 5,985,557 | A | 11/1999 | Prudent et al. | 435/6.1 |
| 5,994,069 | A | 11/1999 | Hall et al. | 435/6.18 |
| 6,001,567 | A | 12/1999 | Brow et al. | 435/5 |
| 6,090,543 | A | 7/2000 | Prudent et al. | 435/6.18 |
| 6,890,741 | B2* | 5/2005 | Fan et al. | 435/91.2 |
| 6,913,884 | B2* | 7/2005 | Stuelpnagel et al. | 435/6.12 |
| 7,361,488 | B2 | 4/2008 | Fan et al. | 435/91.2 |
| 7,582,420 | B2* | 9/2009 | Oliphant et al. | 435/6.12 |
| 7,955,794 | B2* | 6/2011 | Shen et al. | 435/6.11 |
| 2001/0007985 | A1* | 7/2001 | Rothberg et al. | 707/1 |
| 2005/0074774 | A1* | 4/2005 | Woudenberg et al. | 435/6 |
| 2006/0073506 | A1* | 4/2006 | Christians et al. | 435/6 |
| 2007/0259357 | A1* | 11/2007 | Brenner | 435/6 |
| 2009/0004665 | A1* | 1/2009 | Brenner | 435/6 |
| 2009/0098555 | A1* | 4/2009 | Roth et al. | 435/6 |
| 2009/0156424 | A1* | 6/2009 | Thompson | 506/9 |
| 2010/0136557 | A1* | 6/2010 | Brenner | 435/6 |

OTHER PUBLICATIONS

The Stratagene Catalog p. 39 (1988).*
Bevan et al., Sequencing of PCR-amplified DNA PCR Methods and Applications 1 :222 (1992).*
Grabowski P., Alternative splicing in parallel . Nature Biotechnology 20 :346 (2002).*
Johnson et al.,Genome-wide survey of human alternative pre-mRNA splicing with exon junction microarrays. Science 302 : 2141 (2003).*
Pan et al. Deep surveying of alternative splicing complexity in the human transcriptome by high-throughput sequencing. Nature Genetics 40 (12) : 1413 (2008).*
Sultan et al., A global view of gene activity and alternative splicing by deep sequencing of the human transcriptome. Science 321 :956 (2008).*
Wang et al.Alternative isoform regulation in human tissue transcriptomes. Nature 456 :470 (2008).*
Yeakley et al.,Profiling alternative splicing on fiber-optic arrays. Nature Biotechnology 20 : 353 (2002).*
Gad et al., Color Bar Coding the BRCA1 Gene on Combed DNA: A Useful Strategy for Detecting Large Gene Rearrangements. Genes, Chromosomes & Cancer 31 : 75-84 (2001).*
Nilsson et al.RNA-templated DNA ligation for transcript analysis. Nucleic Acids Research 29 (2) :578 (2001).*
Aartsma-Rus, A. and van Ommen, G.-J. B. (2007) Antisense-mediated exon skipping: A versatile tool with therapeutic and research applications, *RNA* 13(10), 1609-1624.
Anderson, M. L. M. and Young, B. D. (1985) Quantitative Filter Hybridization, in *Nucleic Acid Hybridisation; A Practical Approach* (Hames, B. D., and Higgins, S. J., Eds.), pp. 73-111, Oxford University Press, USA.
Ben-Dov, C. et al. (2008) Genome-wide Analysis of Alternative Pre-mRNA Splicing, *Journal of Biological Chemistry* 283(3), 1229-1233.
Back, D. L. (2000) Protein Diversity from Alternative Splicing: A Challenge for Bioinformatics and Post-Genome Biology, *Cell* 103(3), 367-370.
Braslavsky, I. et al. (2003) Sequence information can be obtained from single DNA molecules, *Proc. Natl. Acad. Sci. U. S. A.* 100(7), 3960-3964.
Calarco, J. A. et al. (2007) Technologies for the global discovery and analysis of alternative splicing, *Advances in Experimental Medicine and Biology* 623, 64-84.
Calarco, J. A. et al. (2007) Global analysis of alternative splicing differences between humans and chimpanzees, *Genes & Development* 21(22), 2963-2975.

(Continued)

*Primary Examiner* — Ethan C Whisenant
(74) *Attorney, Agent, or Firm* — Medlen & Carroll, LLP

(57) ABSTRACT

A technology is described that is capable of generating high-throughput sequencing (HTS) read length DNA products to accurately and reliably provide exon connectivity information for alternatively spliced isoforms. The method is not limited by the initial size of the isoform as the technology removes the template oligonucleotide sequence and a newly formed full length ligated product provides an HTS-compatible read length sequence that comprises information that corresponds to the consecutive order of the exons in the original template oligonucleotide.

10 Claims, 22 Drawing Sheets

(56) References Cited

OTHER PUBLICATIONS

Chauhan, A. K. et al. (2004) Alternative splicing of fibronectin: a mouse model demonstrates the identity of in vitro and in vivo systems and the processing autonomy of regulated exons in adult mice, *Gene* 324(0), 55-63.
Church, G. M. (2006) Genomes for All, *Scientific American* 294(1), 46-54.
Conze, T. et al. (2010) Single molecule analysis of combinatorial splicing, *Nucleic Acids Research* 38(16), e163.
Dieffenbach, C. W. and Dveksler, G. S. (1995) *PCR Primer, A Laboratory Manual*, Cold Spring Harbor Laboratory Press, Plainview, N.Y.
Djebali, S. et al. (2008) Efficient targeted transcript discovery via array-based normalization of RACE libraries, *Nature Methods* 5(7), 629-635.
Dou, Y. et al. (2006) Genomic splice-site analysis reveals frequent alternative splicing close to the dominant splice site. *RNA* 12(12), 2047-2056.
Edwards, J. R. et al. (2005) Mass-spectrometry DNA sequencing, *Mutation Research/Fundamental and Molecular Mechanisms of Mutagenesis* 573(1-2), 3-12.
Emerick, M. C. et al. (2007) Multivariate Analysis and Visualization of Splicing Correlations in Single-Gene Transcriptomes, *BMC Bioinformatics* 8, 16-29.
US 5,962,233, 3/1999, Willey, J. C. et al. (withdrawn).
Fagnani, M. et al. (2007) Functional coordination of alternative splicing in the mammalian central nervous system, *Genome Biology* 8(6), R108.
Fan, J.-B. et al. (2004) A Versatile Assay for High-Throughput Gene Expression Profiling on Universal Array Matrices, *Genome Research* 14(5), 878-885.
Fededa, J. P. et al. (2005) A Polar Mechanism Coordinates Different Regions of Alternative Splicing within a Single Gene, *Molecular Cell* 19(3), 393-404.
Gilbert, W. (1978) Why genes in pieces?, *Nature* 271(5645), 501-501.
Grabowski, P. (2002) Alternative splicing in parallel, *Nature Biotechnology* 20(4), 346-347.
Hall, N. (2007) Advanced sequencing technologies and their wider impact in microbiology. *Journal of Experimental Biology* 210(9), 1518-1525.
Hanna, G. J. et al. (2000) Comparison of Sequencing by Hybridization and Cycle Sequencing for Genotyping of Human Immunodeficiency Virus Type 1 Reverse Transcriptase, *Journal of Clinical Microbiology* 38(7), 2715-2721.
Johnson, J. M. et al. (2003) Genome-Wide Survey of Human Alternative Pre-mRNA Splicing with Exon Junction Microarrays, *Science* 302(5653), 2141-2144.
Kim, N. and Lee, C. (2008) Bioinformatics detection of alternative splicing, *Methods in Molecular Biology* 452(179-97).
Kuhn, H. and Frank-Kamenetskii, M. D. (2005) Template-independent ligation of single-stranded DNA by T4 DNA ligase, *FEBS Journal* 272(23), 5991-6000.
Lynch, K. W. (2004) Consequences of regulated pre-mRNA splicing in the immune system, *Nature Reviews Immunology* 4(12), 931-940.
Lynch, K. W. and Weiss, A. (2000) A Model System for Activation-Induced Alternative Splicing of CD45 Pre-mRNA in T Cells Implicates Protein Kinase C and Ras, *Molecular and Cellular Biology* 20(1), 70-80.
Margulies, M. et al. (2005) Genome sequencing in microfabricated high-density picolitre reactors, *Nature* 437(7057). 376-380.
Modrek, B. and Lee, C. (2002) A genomic view of alternative splicing, *Nature Genetics* 30(1), 13-19.
Mortazavi, A. et al. (2008) Mapping and quantifying mammalian transcriptomes by RNA-Seq, *Nature Methods* 5(7), 621-628.
Nilsen, T. W. and Graveley, B. R. (2010) Expansion of the eukaryotic proteome by alternative splicing, *Nature* 463(7280), 457-463.
Nilsson, M. et al. (2001) RNA-templated DNA ligation for transcript analysis. *Nucleic Acids Research* 29(2), 578-581.
Pan, Q. et al. (2006) Quantitative microarray profiling provides evidence against widespread coupling of alternative splicing with nonsense-mediated mRNA decay to control gene expression, *Genes & Development* 20(2), 153-158.
Pan, Q. et al. (2008) Deep surveying of alternative splicing complexity in the human transcriptome by high-throughput sequencing, *Nature Genetics* 40(12), 1413-1415.
Peck, D. et al. (2006) A method for high-throughput gene expression signature analysis, *Genome Biology* 7(7), R61.
Ronaghi, M. et al. (1996) Real-Time DNA Sequencing Using Detection of Pyrophosphate Release, *Analytical Biochemistry* 242(1), 84-89.
Rothberg, J. M. and Leamon, J. H. (2008) The development and impact of 454 sequencing, *Nature Biotechnology* 26(10), 1117-1124.
Rothstein, D. M. et al. (1991) Cyclic regulation of CD45 isoform expression in a long term human CD4+CD45RA+ T cell line, *The Journal of Immunology* 146(4), 1175-1183.
Salehi-Ashtiani, K. et al. (2008) Isoform discovery by targeted cloning, 'deep-well' pooling and parallel sequencing, *Nature Methods* 5(7), 597-600.
Sambrook, J. et al. (1989) in *Molecular Cloning: A Laboratory Manual* (Sambrook, J., Fritsch, E. F., and Maniatis, T., Eds.) 2nd ed., pp. 7.39-37.52, Cold Spring Harbor Laboratory Press, New York.
Sambrook, J. et al. (1989) in *Molecular Cloning: A Laboratory Manual* (Sambrook, J., Fritsch, E. F., and Maniatis, T., Eds.) 2nd ed., pp. 9.31-9.58, Cold Spring Harbor Laboratory Press, New York.
Sambrook, J. et al. (1989) in *Molecular Cloning: A Laboratory Manual* (Sambrook, J., Fritsch, E. F., and Maniatis, T., Eds.) 2nd ed., pp. 16.07-16.08, Cold Spring Harbor Laboratory Press, New York.
Sazani, P. and Kole, R. (2003) Therapeutic potential of antisense oligonucleotides as modulators of alternative splicing. *Journal of Clinical Investigation* 112(4), 481-486.
Sharp, P. A. (1994) Split genes and RNA splicing, *Cell* 77(6), 805-815.
Shendure, J. (2008) The beginning of the end for microarrays?, *Nature Methods* 5(7), 585-587.
Shendure, J. et al. (2005) Accurate multiplex polony sequencing of an evolved bacterial genome, *Science* 309(5741), 1728-1732.
Shendure, J. et al. (2004) Advanced sequencing technologies: methods and goals, *Nature Reviews Genetics* 5(5), 335-344.
Southern, E. M. (2001) DNA Microarrays, History and Overview, *Methods in Molecular Biology* 170, 1-15.
Sultan, M. et al. (2008) A Global View of Gene Activity and Alternative Splicing by Deep Sequencing of the Human Transcriptome, *Science* 321(5891), 956-960.
Tazi, J. et al. (2009) Alternative splicing and disease, *Biochimica et Biophysica Acta (BBA)—Molecular Basis of Disease* 1792(1), 14-26.
Wang, E. T. et al. (2008) Alternative isoform regulation in human tissue transcriptomes, *Nature* 456(7221), 470-476.
White, E. S. et al. (2008) New insights into form and function of fibronectin splice variants, *The Journal of Pathology* 216(1), 1-14.
Xia, T. et al. (1998) Thermodynamic Parameters for an Expanded Nearest-Neighbor Model for Formation of RNA Duplexes with Watson-Crick Base Pairs, *Biochemistry* 37(42), 14719-14735.
Yang, L. et al. (2001) BADGE, BeadsArray for the Detection of Gene Expression, a High-Throughput Diagnostic Bioassay, *Genome Research* 11(11), 1888-1898.
Yeakley, J. M. et al. (2002) Profiling alternative splicing on fiber-optic arrays, *Nature Biotechnology* 20(4), 353-358.
Zheng, C. L. et al. (2004) A database designed to computationally aid an experimental approach to alternative splicing, *Pacific Symposium on Biocomputing. Pacific Symposium on Biocomputing* 9, 78-88.
Zhu, J. et al. (2003) Single Molecule Profiling of Alternative Pre-mRNA Splicing, *Science* 301(5634). 836-838.
US 5,962,233, 10/1999, Livak et al. (withdrawn)

* cited by examiner

| Gene name | Key | nt of mRNA between exons | possible isoforms |
|---|---|---|---|
| Chl1* | C | 4665 | 18 |
| Mdm1 | M | 1846 | 4 |
| PTPRF-Y | Y | 1633 | 4 |
| Cacna1c | Ca | 1403 | 4 |
| PTPRF-X | X | 936 | 4 |
| FN1 | F | 813 | 8 |
| Apbb1* | A | 802 | 260 |
| Agrn | G | 736 | 8 |
| Exoc7 | E | 513 | 4 |
| Prom1 | P | 512 | 4 |
| Lphn2 | L | 396 | 32 |
| * = promoter usage examined | | | 350 |

```
SEQUENCE LISTING

<160> NUMBER OF SEQ ID NOS: 27

<210> SEQ ID NO 1
<211> LENGTH: 38
<212> TYPE: DNA
<213> ORGANISM: Mus musculus

<400> SEQUENCE: 1 atagggcac tttccttgtc tgagcgggct ggcaaggc                          38

<210> SEQ ID NO 2
<211> LENGTH: 20
<212> TYPE: DNA
<213> ORGANISM: Mus musculus

<400> SEQUENCE: 2
ctgggacaac ggtatcagag                                              20

<210> SEQ ID NO 3
<211> LENGTH: 41
<212> TYPE: DNA
<213> ORGANISM: Mus musculus

<400> SEQUENCE: 3
ccgtttgctg tgtcagtgtc atcaagtgag ctggggcacc t                     41

<210> SEQ ID NO 4
<211> LENGTH: 38
<212> TYPE: DNA
<213> ORGANISM: Mus musculus

<400> SEQUENCE: 4
```

```
gcctccctcg cgccatcaga ccgtgggagg agggacag                              38
```

<210> SEQ ID NO 5
<211> LENGTH: 44
<212> TYPE: DNA
<213> ORGANISM: Mus musculus

<400> SEQUENCE: 5

```
tggtcactgc agtttgaacc tcatcaccgt gggaggaggg acag                       44
```

<210> SEQ ID NO 6
<211> LENGTH: 47
<212> TYPE: DNA
<213> ORGANISM: Mus musculus

<400> SEQUENCE: 6

```
tggtcactgc agtttgaacc atcatcatct gagcgggctg gcaaggc                    47
```

<210> SEQ ID NO 7
<211> LENGTH: 50
<212> TYPE: DNA
<213> ORGANISM: Mus musculus

<400> SEQUENCE: 7

```
ctgtggactg gattccaatc atcatcacag tcctttaggg cgatcaatgt                 50
```

<210> SEQ ID NO 8
<211> LENGTH: 44
<212> TYPE: DNA
<213> ORGANISM: Mus musculus

<400> SEQUENCE: 8

```
ctgtcttctt cctcccaatc agggtcatca gggcgcagga atgg                       44
```

<210> SEQ ID NO 9
<211> LENGTH: 39
<212> TYPE: DNA
<213> ORGANISM: Mus musculus

<400> SEQUENCE: 9

```
ctgtggaggg aacatctcat cacagttggg gaagctcat                             39
```

<210> SEQ ID NO 10
<211> LENGTH: 51
<212> TYPE: DNA
<213> ORGANISM: Mus musculus

<400> SEQUENCE: 10

```
ctgtagaggc atttggattg aggtcatcag tgatgaaggg ggtcttttga a               51
```

<210> SEQ ID NO 11
<211> LENGTH: 44
<212> TYPE: DNA
<213> ORGANISM: Mus musculus

<400> SEQUENCE: 11

```
gcctccctcg cgccatcaga tcatcagaga gagagcttcc tgtc                       44
```

<210> SEQ ID NO 12
<211> LENGTH: 24
<212> TYPE: DNA
<213> ORGANISM: Mus musculus

<400> SEQUENCE: 12
ctgtcttctt cctcccaatc aggg                                    24

<210> SEQ ID NO 13
<211> LENGTH: 53
<212> TYPE: DNA
<213> ORGANISM: Mus musculus

<400> SEQUENCE: 13
gctcactctt ctgattgttc ttcagggtca tcatctgagc gggctggcaa ggc    53

<210> SEQ ID NO 14
<211> LENGTH: 15
<212> TYPE: DNA
<213> ORGANISM: Mus musculus

<400> SEQUENCE: 14
tgggcgcagg aatgg                                              15

<210> SEQ ID NO 15
<211> LENGTH: 52
<212> TYPE: DNA
<213> ORGANISM: Mus musculus

<400> SEQUENCE: 15
gcctccctcg cgccatcaga tcatcatgtc acctgactga acttcagatt gg     52

<210> SEQ ID NO 16
<211> LENGTH: 41
<212> TYPE: DNA
<213> ORGANISM: Mus musculus

<400> SEQUENCE: 16
gcctccctcg cgccatcaga catgagtcct gacacaatca c                 41

<210> SEQ ID NO 17
<211> LENGTH: 57
<212> TYPE: DNA
<213> ORGANISM: Mus musculus

<400> SEQUENCE: 17
cactgacttc gtatttagtg gccactcatc acctgttctg atcaatgaca tctacaa 57

<210> SEQ ID NO 18
<211> LENGTH: 37
<212> TYPE: DNA
<213> ORGANISM: Mus musculus

<400> SEQUENCE: 18
ggtccatcca ctaaagctct gagcgggctg gcaaggc                      37

<210> SEQ ID NO 19
<211> LENGTH: 56
<212> TYPE: DNA
<213> ORGANISM: Homo sapiens

<400> SEQUENCE: 19
gcctccctcg cgccatcaga tcgtaggcac ctgaaagggc tcagagtggt tgtttc 56

<210> SEQ ID NO 20
<211> LENGTH: 20
<212> TYPE: DNA
<213> ORGANISM: Homo sapiens

```
<400> SEQUENCE: 20
agaggcatta aggtaggcat                                              20

<210> SEQ ID NO 21
<211> LENGTH: 38
<212> TYPE: DNA
<213> ORGANISM: Homo sapiens

<400> SEQUENCE: 21
ctgaggtgtt cgctgtcatc acctctctcc tgggacat                          38

<210> SEQ ID NO 22
<211> LENGTH: 44
<212> TYPE: DNA
<213> ORGANISM: Homo sapiens

<400> SEQUENCE: 22
ctgagatagc attgctgctc atcacgtctg tactgatgaa acac                   44

<210> SEQ ID NO 23
<211> LENGTH: 46
<212> TYPE: DNA
<213> ORGANISM: Homo sapiens

<400> SEQUENCE: 23
ctgtggtatt aaaagcacta tcatcacatc tttgctgtag tcaatc                 46

<210> SEQ ID NO 24
<211> LENGTH: 56
<212> TYPE: DNA
<213> ORGANISM: Homo sapiens

<400> SEQUENCE: 24 cagtgggga aggtgttggg ctgtaggcac catcaatctg agcgggctgg caaggc       56

<210> SEQ ID NO 25
<211> LENGTH: 42
<212> TYPE: RNA
<213> ORGANISM: Homo sapiens

<400> SEQUENCE: 25
auagugcuuu uaauaccaca gguguuucau caguacagac gu                     42

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
ctgtggtatt aaaagcacta t                                            21

<210> SEQ ID NO 27
<211> LENGTH: 21
<212> TYPE: DNA
<213> ORGANISM: Artificial Sequence
<220> FEATURE:
<223> OTHER INFORMATION: Synthetic

<400> SEQUENCE: 27
acgtctgtac tgatgaaaca c                                            21
```

DEDUCING EXON CONNECTIVITY BY RNA-TEMPLATED DNA LIGATION/SEQUENCING

FIELD OF INVENTION

The present invention is related to the field of genomics. For example, compositions and methods are described that are useful in determining intra- or intergene relationships such that physically distant exons may act in concert. Such exon coordination may be determined by using techniques that are capable of creating, ligating, and identifying oligonucleotides that reflect functional exon connectivity. These oligonucleotides comprise ligamers having a plurality of binding sites, wherein each binding site is complementary with a different exon.

BACKGROUND

As the number of predicted human genes has decreased, estimates of the extent of alternative pre-mRNA splicing have increased dramatically. Ninety-six percent of multi-exon human genes are thought to be alternatively spliced, generating a diversity of proteins far larger than the number of human genes. Pan et al., "Deep surveying of alternative splicing complexity in the human transcriptome by high-throughput sequencing" Nature Genetics 40:1413-1415 (2008); and Wang et al., "Alternative isoform regulation in human tissue transcriptomes" Nature 456:470-476 (2008). Large-scale sequencing of fragmented mRNA (RNA-Seq) confirms this view: 114,742 different exon-exon junctions have been detected in human brain alone. However, RNA-Seq does not preserve the connectivity between exon-exon junction fragments, so that the potential influence of one splicing event on subsequent splicing events in the same transcript cannot be detected. Calarco et al., "Technologies for the global discovery and analysis of alternative splicing" Advances in Experimental Medicine and Biology 623:64-84 (2007). In the mouse central nervous system, the splicing of some pairs of exons appears to be coordinated. Fagnani et al., "Functional coordination of alternative splicing in the mammalian central nervous system" Genome Biology 8:R108-R108 (2007). Currently, the scope of such interdependence between distant splicing events is unknown.

Complex organisms increase the effective diversity and coding potential of their genomes through alternative splicing (AS). With the advent of newly developed high-throughput sequencing (HTS) techniques, it is estimated that 86% of multi-exon human genes undergo AS. A unique product of an AS event is called an isoform. The sheer number of isoforms detected by these studies, often expressed in a tissue-specific manner, suggests that AS may have biological significance.

While it has been estimated that approximately 25% of human genes contain multiple regions of AS, the coordination of different regions in the same mRNA molecule has been suggested for less than 40 genes and confirmed in even fewer. Types of AS include, for example, alternative transcriptional start sites, polyadenylation sites and/or first & last exons. Undoubtedly, inherent restrictions of methods used for the large-scale study of isoforms contribute to difficulties in identifying and studying distal coordinated AS events.

Most methods used for the large-scale study of isoforms involve, at some point, microarrays and/or sequencing. One common limitation is the piecemeal examination of a potentially long molecule. Isoforms can be many tens of thousands of nucleotides (nt) long, yet microarrays and sequencing can only analyze between 25 and 1000 nt of that sequence at one time. This limitation forces the reconstruction of the original sequence, during which the connectivity of sequence for a given molecule is lost, severely limiting the determination of splicing regulation that may occur over a distance. While it is possible to investigate coordinated AS in a single gene through traditional cloning and RT-PCR analysis, using these approaches in a large-scale study is very labor-intensive.

However, a high-throughput, single-molecule technique, designed to directly assay distal regions of AS, may provide evidence for a general phenomenon of coordinated, intramolecular, splicing choices. It is clear that a more informative method to assess alternative splicing across the genome is needed. For example, a method that establishes exon sequence connectivity for each mRNA isoform in a cell, retains abundance information, and uses existing HTS technology would be advantageous to the molecular biology research community.

SUMMARY OF THE INVENTION

The present invention is related to the field of genomics. For example, compositions and methods are described that are useful in determining intra- or intergene relationships such that physically distant exons may act in concert. Such exon coordination may be determined by using techniques that are capable of creating and ligating oligonucleotides that reflect functional exon connectivity. These oligonucleotides comprise joined ligamers having a plurality of binding sites, wherein each binding site is complementary with a different exon.

In one embodiment, the present invention contemplates a composition comprising a ligamer comprising a single barcode sequence and a plurality of complementarity regions. In one embodiment, each of the complementarity regions comprise a different nucleotide sequence. In one embodiment, the composition further comprises a template oligonucleotide comprising a plurality of hybridization sites. In one embodiment, the template oligonucleotide hybridization sites are complementary to the complementarity regions. In one embodiment, the template oligonucleotide comprises an mRNA oligonucleotide. In one embodiment, the mRNA oligonucleotide comprises a plurality of exons. In one embodiment, the hybridization sites comprise a flanking region of the exons. In one embodiment, the barcode sequence is non-complementary to the exon. In one embodiment, the ligamer comprises between approximately 5-5,000 nt. In one embodiment, the ligamer comprises between approximately 10-3,000 nt. In one embodiment, the ligamer comprises between approximately 20-1,000 nt.

In one embodiment, the present invention contemplates a method comprising, a) providing: i) a plurality of ligamers, wherein each of the ligamers comprise a single different barcode sequence and a plurality of different complementarity regions; and ii) a template oligonucleotide, wherein the oligonucleotide comprises a plurality of hybridization sites; b) mixing the plurality of ligamers with the template oligonucleotide under conditions such that the complementarity regions bind to the hybridization sites; c) ligating the ligamers to create a full length ligated product (FLLP); d) amplifying the FLLP under conditions to create a DNA product; e) identifying the consecutive order of the barcodes within the DNA product. In one embodiment, the template oligonucleotide comprises an mRNA oligonucleotide. In one embodiment, the mRNA oligonucleotide comprises a plurality of exons. In one embodiment, each of the barcodes corresponds to one of the exons. In one embodiment, the identifying comprises nucleotide sequencing.

In one embodiment, the present invention contemplates a composition comprising at least one oligonucleotide (i.e., a ligamer) comprising two distinct regions of complementarity to a template mRNA sequence (i.e., for example, an mRNA). In one embodiment, the template mRNA sequence comprises a first and second exon. In one embodiment, a first ligamer comprises a first complementary region that hybridizes to a 5' edge of said first exon. In one embodiment, the first ligamer comprises a second complementary region that hybridizes to a 3' edge of the first exon. In one embodiment, a second ligamer comprises a third complementary region that hybridizes to a 5' edge of said second exon. In one embodiment, the second ligamer comprises a forth complementary region that hybridizes to a 3' edge of the second exon. In one embodiment, the first and second exons are adjacent. In one embodiment, multiple ligamers are adjacently hybridized to the same transcript and joined enzymatically (i.e., for example, ligated), thereby creating a joined oligonucleotide. In one embodiment, the joined oligonucleotide directly reflects the presence of the first exon and second exon. In one embodiment, the first exon is located on a first gene and a second exon is located on a second gene, wherein said first and second exons become adjacent following splicing.

In one embodiment, the present invention contemplates a method of establishing exon sequence connectivity, comprising: a) providing: i) a plurality of ligamers, each of said ligamers comprising a portion that is non-complementary to a specific exon (functioning as a bar code), said portion separating two regions of complementarity to the flanking regions of said specific exon, ii) a target mRNA molecule, and iii) ligase; b) mixing said ligamers and said target mRNA under conditions such that at least a portion of said ligamers hybridize to said target mRNA; c) ligating the 5' and 3' ends of adjacent ligamers hybridized to said mRNA target to create a DNA product; and d) digesting said mRNA target. In one embodiment, the target mRNA is an alternatively spliced isoform of a multi-exon nucleotide sequence. In one embodiment, the target mRNA is from total cellular RNA. In one embodiment, the method further comprises step (e) amplifying said DNA product. In one embodiment, the method further comprises step (f) determining the bar code sequence of said DNA product. In one embodiment, the method further comprises step (g) determining the relative abundance of various bar coded DNA products.

In one embodiment, the present invention contemplates a kit, comprising: a) a first container comprising a plurality of ligamers, wherein each of said ligamers comprise a single different barcode sequence and a plurality of different complementarity regions; and b) a second container comprising a template oligonucleotide, wherein said oligonucleotide comprises a plurality of hybridization sites; c) a third container comprising buffers and reagents for hybridizing said ligamers and template oligonucleotide; d) a fourth container comprises a ligase and associated buffers and reagents; and, e) a set of instructions for; i) hybridizing said ligamers and said template oligonucleotide; and ii) ligating said ligamers to create a full length ligated product.

In one embodiment, the present invention contemplates a method comprising a cost-effective and practical approach capable of a complete gene expression analysis. In one embodiment, the method is compatible with basic research techniques.

In one embodiment, the present invention contemplates a method comprising a patient exhibiting at least one symptom of a disease and/or medical condition. In one embodiment, the disease and/or medical condition is diagnosed by identifying a cancer, condition, or disease-specific AS isoform.

DEFINITIONS

The term "ligamer" as used herein, refers to any oligonucleotide comprising a central region having an exon-specific bar code (i.e., for example, such as a unique, natural or non-natural nucleic acid sequence that can be identified to correspond to specific exons for unambiguous identification) and at least two complementary regions, wherein each complementary region comprises a different nucleotide sequence. For example, a complementary region may comprise between approximately 8-20 amino acid sequences flanking each end of the ligamer, nonetheless a desired $T_m$ determines the optimal ligamer length. Ligamers may include, but are not limited to, natural or unnatural nucleic acids.

The term "exon connectivity" as used herein, refers to the particular arrangement of exons over the entire length of a single transcript and/or the influence of one exon on (an)other exon(s) to be included in a particular alternative splice, whether the respective exons reside within the same, or different, gene(s).

The term "barcode" as used herein, refers to a specific nucleic acid sequence (i.e., for example, including, but not limited to, natural or unnatural nucleotides) that provides an unambiguous identifier code.

The term "complementarity regions", as used herein, refer to any nucleotide sequence on a ligamer that is capable of hybridizing to a template oligonucleotide. For example, if the template oligonucleotide comprises an mRNA sequence having a plurality of exons, the complementarity regions hybridize with exon flanking sequences.

The term "different sequence" as used herein, refers to a comparison of at least two separate oligonucleotides that are not capable of hybridizing to the same nucleic acid sequence.

The term "template oligonucleotide" as used herein, refers to any oligonucleotide capable of hybridizing with a set of ligamers. For example, a template oligonucleotide may comprise mRNA having a plurality of exons.

The term "flanking region" as used herein, refers to any nucleotide sequence residing on a template oligonucleotide that is capable of hybridizing to a ligamer complementarity region.

The term "ligate" or "ligation" as used herein, refers to any joining of at least two nucleic acids. Such a joining may occur spontaneously (i.e., for example, self-ligation) exemplified by the self-ligation of ligamers described herein that may undergo ligation when being placed adjacent to one another (i.e., lined-up together). Alternatively, ligation may be mediated either enzymatically (i.e., for example, by a protein ligase such as RNL2) or a chemical reaction that joins (i.e., links) the nucleic acids together.

The term "a full length ligated product" as used herein, refers to a plurality of ligamers that have been ligated into a single oligonucleotide.

The term "a DNA product" as used herein, refers to any oligonucleotide that results from PCR amplification of a full length ligation product. For example, a DNA product may have a length compatible with HTS devices (i.e., for example, 35-800 nt).

The term "exon junction" or "splice junction" as used herein, refers to a locus where two exons are joined together after splicing.

The term, "purified" or "isolated", as used herein, may refer to a nucleic acid or oligonucleotide composition that has been subjected to treatment (i.e., for example, fractionation) to remove various other components, and which composition substantially retains its expressed biological activity. Where the term "substantially purified" is used, this designation will refer to a composition in which the nucleic acid or oligonucleotide forms the major component of the composition, such as constituting about 50%, about 60%, about 70%, about 80%, about 90%, about 95% or more of the composition (i.e., for example, weight/weight and/or weight/volume). The term "purified to homogeneity" is used to include compositions that have been purified to 'apparent homogeneity" such that there is single oligonucleotide species (i.e., for example, based upon SDS-PAGE or HPLC analysis). A purified composition is not intended to mean that some trace impurities may remain.

As used herein, the term "substantially purified" refers to molecules, such as nucleic acid sequences, that are removed from their natural environment, isolated or separated, and are at least 60% free, preferably 75% free, and more preferably 90% free from other components with which they are naturally associated. An "isolated polynucleotide" is therefore a substantially purified polynucleotide.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand. Nucleic acid sequence are believed to comprise nucleic acids (either natural or unnatural) either with or without sugar modifications, and optionally, alternative backbone structures. For example, alternative backbone structures may include, but are not limited to, phosphoramide, phosphorothioate, O-methylphosphoroamidite, peptide nucleic acid, positively charged backbones, non-ionic backbones, or non-ribose backbones.

The term "an isolated nucleic acid", as used herein, refers to any nucleic acid molecule that has been removed from its natural state (e.g., removed from a cell and is, in a preferred embodiment, free of other genomic nucleic acid). A nucleic acid may be a natural nucleic acid or an unnatural nucleic acid, and optionally may have sugar modifications. For example, a nucleic acid base may include, but is not limited to, uracil, adenine, thymine, cytosine, guanine, inosine, xanthanine hypoxathanine, iocytosine, isoguanine, universal base's, diaminopurine, or tricyclic Aminoethyl-Phenoxazine 2'-deoxyCytidine (AP-dC, G-Clamp). For example, a sugar modification may include, but not be limited to 2'O Methyl (2'Ome), and locked nucleic acids (LNA).

The term "portion" when used in reference to a nucleotide sequence refers to fragments of that nucleotide sequence. The fragments may range in size from 5 nucleotide residues to the entire nucleotide sequence minus one nucleic acid residue.

As used herein, the term "antisense" is used in reference to RNA sequences which are complementary to a specific RNA sequence (e.g., mRNA). Antisense RNA may be produced by any method, including synthesis by splicing the gene(s) of interest in a reverse orientation to a viral promoter which permits the synthesis of a coding strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables). For example, a pulmonary sample may be collected by bronchoalveolar lavage (BAL) which comprises fluid and cells derived from lung tissues. A biological sample may comprise a cell, tissue extract, body fluid, chromosomes or extrachromosomal elements isolated from a cell, genomic DNA (in solution or bound to a solid support such as for Southern blot analysis), RNA (in solution or bound to a solid support such as for Northern blot analysis), cDNA (in solution or bound to a solid support) and the like.

The term "functionally equivalent codon", as used herein, refers to different codons that encode the same amino acid. This phenomenon is often referred to as "degeneracy" of the genetic code. For example, six different codons encode the amino acid arginine.

A "variant" of a nucleotide is defined as a novel nucleotide sequence which differs from a reference oligonucleotide by having deletions, insertions and substitutions. These may be detected using a variety of methods (e.g., sequencing, hybridization assays etc.).

A "deletion" is defined as a change in a nucleotide or oligonucleotide sequence in which one or more nucleotides or amino acid residues, respectively, are absent.

An "insertion" or "addition" is that change in a nucleotide or oligonucleotide sequence which has resulted in the addition of one or more nucleotide residues.

A "substitution" results from the replacement of one or more nucleotides by different nucleotides.

The term "derivative" as used herein, refers to any chemical modification of a nucleic acid. Illustrative of such modifications would be replacement of hydrogen by an alkyl, acyl, or amino group.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "C-A-G-T," is complementary to the sequence "G-T-C-A." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. This is of particular importance in amplification reactions, as well as detection methods which depend upon binding between nucleic acids.

The terms "homology" and "homologous" as used herein in reference to nucleotide sequences, refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

The terms "homology" and "homologous" as used herein in reference to amino acid sequences refer to the degree of identity of the primary structure between two amino acid sequences. Such a degree of identity may be directed a portion of each amino acid sequence, or to the entire length of the amino acid sequence. Two or more amino acid sequences that are "substantially homologous" may have at least 50% identity, preferably at least 75% identity, more preferably at least 85% identity, most preferably at least 95%, or 100% identity.

An oligonucleotide sequence which is a "homolog" of a reference oligonucleotide sequence is defined herein as an oligonucleotide sequence which exhibits greater than or equal to 50% identity to the reference oligonucleotide sequence when such sequences having a length of 100 bp or larger are compared.

The term "low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent {50× Denhardt's contains per 500 ml: 5 g Ficoll (Type 400, Pharmacia), 5 g BSA (Fraction V; Sigma)} and 100 µg/ml denatured salmon sperm DNA followed by washing in a solution comprising 5×SSPE, 0.1% SDS at 42° C. when a probe of about 500 nucleotides in length. is employed. Numerous equivalent conditions may also be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) may also be used.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. As indicated by standard references, a simple estimate of the $T_m$ value may be calculated by the equation: $T_m=81.5+0.41$ (% G+C), when a nucleic acid is in aqueous solution at 1M NaCl. Anderson et al., "Quantitative Filter Hybridization" In: *Nucleic Acid Hybridization* (1985). More sophisticated computations take structural, as well as sequence characteristics, into account for the calculation of $T_m$.

As used herein the term "stringency" is used in reference to the conditions of temperature, ionic strength, and the presence of other compounds such as organic solvents, under which nucleic acid hybridizations are conducted. "Stringency" typically occurs in a range from about $T_m$ to about 20° C. to 25° C. below $T_m$. A "stringent hybridization" can be used to identify or detect identical polynucleotide sequences or to identify or detect similar or related polynucleotide sequences. Alternatively, when conditions of "weak" or "low" stringency are used hybridization may occur with nucleic acids that are derived from organisms that are genetically diverse (i.e., for example, the frequency of complementary sequences is usually low between such organisms).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Amplification" is defined as the production of additional copies of a nucleic acid sequence and is generally carried out using polymerase chain reaction. Dieffenbach C. W. and G. S. Dveksler (1995) In: *PCR Primer, a Laboratory Manual*, Cold Spring Harbor Press, Plainview, N.Y.

As used herein, the term "polymerase chain reaction" ("PCR") refers to the method of K. B. Mullis U.S. Pat. Nos. 4,683,195 and 4,683,202, herein incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxy-ribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers; to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "an oligonucleotide having a nucleotide sequence encoding a gene" means a nucleic acid sequence comprising the coding region of a gene, i.e. the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The presence of "splicing signals" on an expression vector often results in higher levels of expression of the recombinant transcript. Splicing signals mediate the removal of introns from the primary RNA transcript and consist of a splice donor and acceptor site. Sambrook, J. et al., In: *Molecular Cloning: A Laboratory Manual*, 2nd ed., Cold Spring Harbor laboratory Press, New York (1989) pp. 16.7-16.8. A commonly used splice donor and acceptor site is the splice junction from the 16S RNA of SV40.

The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. Efficient expression of recombinant DNA sequences in eukaryotic cells involves expression of signals directing the efficient termination and polyadenylation of the resulting transcript. Transcription termination signals are generally found downstream of the polyadenylation signal and are a few hundred nucleotides in length.

As used herein, the terms "nucleic acid molecule encoding", "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "Southern blot" refers to the analysis of DNA on agarose or acrylamide gels to fractionate the DNA according to size, followed by transfer and immobilization of the DNA from the gel to a solid support, such as nitrocellulose or a nylon membrane. The immobilized DNA is then probed with a labeled oligodeoxyribonucleotide probe or DNA probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists. J. Sambrook et al. (1989) In: *Molecular Cloning: A Laboratory Manual*, Cold Spring Harbor Press, NY, pp 9.31-9.58.

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled oligodeoxyribonucleotide probe or DNA probe to detect RNA species complementary to the probe used. Northern blots are a standard tool of molecular biologists. J. Sambrook, J. et al. (1989) supra, pp 7.39-7.52.

The term "reverse Northern blot" as used herein refers to the analysis of DNA by electrophoresis of DNA on agarose gels to fractionate the DNA on the basis of size followed by transfer of the fractionated DNA from the gel to a solid support, such as nitrocellulose or a nylon membrane. The immobilized DNA is then probed with a labeled oligoribonucleotide probe or RNA probe to detect DNA species complementary to the ribo probe used.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "gene" means the deoxyribonucleotide sequences comprising the coding region of a structural gene and including sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogeneous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "binding" as used herein, refers to any interaction between an infection control composition and a surface. Such as surface is defined as a "binding surface". Binding may be reversible or irreversible. Such binding may be, but is not limited to, non-covalent binding, covalent bonding, ionic bonding, Van de Waal forces or friction, and the like. An infection control composition is bound to a surface if it is impregnated, incorporated, coated, in suspension with, in solution with, mixed with, etc.

The term 'transcript' as used herein, refers to any product of cellular transcription machinery, be it from any of the known, or unknown RNA polymerases (i.e., for example, RNA POL I and/or II). This transcript is composed of ribonucleic acids and may be in either the pre-mRNA (i.e. for example, containing introns), partially or completely processed mRNA state (i.e., for example, some or all introns removed, and/or containing 7-methyl-G cap or poly A sequences). The transcript may be located anywhere within a cell (i.e., for example, in the nucleus or cytoplasm).

The term 'isoform' as used herein, refers to any potential combinations of exons resulting from a single gene and/or multiple genes that share some sequence content. For example, a gene containing three exons, where the first exons may or may not be included in the final 'transcript' could have two potential isoforms. Isoforms can also result from unique arrangements of exons resulting from differently annotated genes, being not obviously joined during initial transcription, but perhaps joined during the processes of splicing.

BRIEF DESCRIPTION OF THE FIGURES

FIG. 1 presents an illustrative schematic of an exon connectivity analysis performed by one embodiment of the present invention (i.e., for example, RNA-templated ligation of barcoded oligodeoxynucleotides).

FIG. 2A: A model mRNA transcript is illustrated comprising a cassette exon AS region (yellow) and two mutually exclusive alternative exons (blue and red) separated by one to five thousand nucleotides.

FIG. 2B: A read length limitation is demonstrated wherein no current method can 'connect' two regions separated by >1500 nt in a single read (i.e., Sanger maximum read length ~900 nt. 454 maximum read length ~400-800 nt. Illumina/SOLiD maximum read length ~30 to 150 nt.) Read lengths are mapped to scale on a typical mRNA.

FIG. 2C: One embodiment of the present invention is shown that 'compresses' the AS pattern by looping out constitutively expressed transcript regions (upper two green exons) that creates a joined oligonucleotide compatible with traditional or high throughput sequence technologies. HTS maximum read length ~800 nt.

FIG. 3A: A schematic of AS regions in a mouse fibronectin. A 5' promoter is depicted (double open rectangles on the left side). Exon EDB (reported elsewhere as EDII) and exon EDA (reported elsewhere as EDI) represent two separate cassette exons involved in fibronectin AS events. Exon IIICS (reported elsewhere as V) is an AS region containing three (3) different 3' Splice Sites (3' SS) represented as separate dark regions. Predicted fibronectin AS nucleotides may encode: i) a first AS comprising a 120 amino acid peptide encoded by EDB, EDA, and IIICS; ii) a second AS comprising a 90 amino acid peptide encoded by IIICS; and iii) an AS comprising a 0 amino acid peptide wherein EDB, EDA, and IIICS are absent. (Chauhan et al., 2004)

FIG. 3B: A schematic showing three mouse fibronectin minigene constructs wherein two EDI exons were inserted (notated as proximal and distal, respectively) that were either wild-type (wt) or modified (notated as ΔESE: denoted by a white or black cross). First minigene construct: pFN-EDI$^{WT}$/EDI$^{WT}$); Second minigene construct: pFN-EDI$^{\Delta ESE}$/EDI$^{WT}$; Third minigene construct: pFN-EDI$^{WT}$/EDI$^{\Delta ESE}$. Three constitutively spliced exons (notated as a triple ring, a rectangle, and a double square) were placed in-between the proximal and distal EDI exons. The data is expressed as a specific AS isoform:promoter densitometry ratio.

FIG. 3C: Demonstrates coordinated AS production in a knock-out mouse model. EDA$^{+/+}$; homozygous wild type genotype. EDA$^{-/-}$: homozygous mutated knock-out genotype.

FIG. 3D: Demonstrates an allele specific RT-PCR strategy in EDA$^{+/-}$ heterozygous knock-out mice.

FIG. 4 illustrates the technique of RNA-mediated annealing, selection, and ligation (RASL) that distinguishes alternative splicing patterns between two biological samples.

FIG. 13A: An exemplary ligamer scheme to assay possible exon coordination between the EDI/A and IIICS/V regions of mouse fibronectin. This set of ligamers may utilize exons 32 and 40A' as 'constitutive' exons. Also, one ligamer will force exons 34 through 39 to loop out.

FIG. 13B: Representative combinations of EDA and IIICS exon inclusions. Using a set of ligamers shown in FIG. 13A, the number of ligation events that may be used for FLLP production is shown. The length (nt) of each FLLP differ enough from each other to observe each as a unique band on a denaturing PAGE gel.

FIG. 15A: Illustrates that the fourth, fifth, and sixth exons of the human CD45 gene may participate in alternative splicing. The third and seventh exons are, however, constitutively included into all isoforms of CD45.

FIG. 15B: One embodiment of an exon connectivity SeqZip workflow:
1) PolyA RNA is obtained from a sample of interest. The PolyA RNA is left on oligo-dT magnetic beads.
2) DNA ligamers are designed and synthesized. The ligamers are mixed appropriately.
3) DNA ligamers are hybridized to the polyA selected mRNA on the beads.
4) Ligamers are joined enzymatically, converting relevant RNA sequence content into a full templated ligation (FTL) product.
5) Using common sequences included in ligamers targeting the 5' and 3' most regions of an RNA, FTL products are amplified.
6) Amplified ligation products are analyzed. For example, the absence of the sequence (or relevant length) corresponding to ligamer 4 demonstrates the absence of exon 4 in the original message.

FIG. 16A: A schematic showing a representative experimental setup. Twenty (20) nucleotide DNA oligos were end-labeled with γ-ATP. These oligos were fully complementary to an in vitro transcribed RNA and hybridized adjacently. The RNA was 100 nt in length, allowing for 5 possible hybridization events per template.

FIG. 16B: A screen of various ligases was performed. Ligases were incubated with either an RNA or DNA template and a common pool of end-labeled DNA oligos. DNA templates were ~80 nt long and accommodated ~4 oligos. Successful ligation was visualized as products of 40, 60, 80, and 100 nucleotides in size. The doublet visible at 20 and 40 nucleotides represents the intermediate adenylated oligos. The viability of each enzyme is confirmed using the DNA template. Of note is Rnl2s inability to create ligation products longer than 40 nt using a DNA template.

FIG. 16C: A ligation time course was performed for Rnl2 and T4 DNA ligase. Non-templated ligation products are annotated as "x-6*" as there are only five (5) hybridization sites on the RNA template.

FIG. 17A: PolyA RNA was obtained from U-937 (U) and Jurkat (J) human T-cell lines. RNA from these two samples were also mixed (U&J). RT-PCR was performed on this RNA to observe expressed isoforms of CD45 (see methods). Observed isoforms of CD45 are on the right as R###, where # refers to which cassette exon is included in the transcript.

FIG. 17B: Using the same polyA selected RNA obtained in FIG. 17A, CD45 isoforms were profiled using SeqZip.

FIG. 17C: A mirror image representation of lane profiles from the U&J samples as shown in FIGS. 17A and 17B.

FIG. 17D: Annotated CD45 isoform bands as shown in FIGS. 17A and 17B were quantified for each sample using the ImageQuant® Software.

FIG. 18A: A schematic illustration showing one embodiment for an experimental setup. Four different in vitro transcribed RNAs were created by amplification of a common 1046 bp plasmid sequence using 4 different PCR primers. Each RNA contained a signature pair of flanking sequences. These RNAs were incubated pairwise to investigate trans-transcript hybridization of a common ligamer targeting the common sequence. Resulting ligation products differed in size as shown.

FIG. 18B: The ABC and DBE RNAs were spiked in a 1:1 ratio across different concentrations in the same background of polyA RNA. A common pool of ligamers were added and SeqZip was performed. The resulting ligation products were amplified with 40 cycles of PCR and run out on a native acrylamide gel. The appearance of trans-transcript ligation products is clearly concentration dependent. Similar results are observed when the opposite pair of in vitro RNAs is used.

FIG. 18C: Ligation products were amplified with a limiting number of PCR cycles to stay in the quantitative range of amplification using a common end-labeled PCR primer. Products were analyzed on an acrylamide gel. Results demonstrate that even at high concentrations of RNA spikes, hybridization of ligamers in cis is the favored interaction.

FIG. 19A: Illustrates that a mouse fibronectin gene (Fn1) is alternatively spliced at cassette EDA (Fn1 A) exon and at the Variable (Fn1 V) region. Splicing at the Fn1 V region utilizes three different 3' splice sites, producing isoforms coding for 120, 95, and 0 additional amino acids. SeqZip can examine AS at these sites using individual ligamer sets, or a combination set. The difference between the two sets is whether or not the intervening sequence of RNA between exon 34 and 39, which is 813 nt in the mRNA, is looped out with a single ligamer.

FIG. 19B: Semi-quantitative PCR of ligation products from Fn1 A and Fn1 V individual ligamer sets or the Fn1 (AV) combination using primary mouse embryonic fibroblast (MEF) cells for input RNA. Isoforms are annotated according to diagram in FIG. 19A.

FIG. 19C: Relative Fn1 isoform abundances in percent of primary MEF cell RNA. Values for inset graph 'observed' (blue bars) were derived from Fn1 A and Fn1 V band intensities corresponding to different AS isoforms as shown in FIG. 19B. The observed values for the main graph were derived from the Fn1 (AV) band intensities. The 'expected' values (red bars) represent the product of the frequencies derived from inset graph observed values. Errors bars represent standard deviation.

FIG. 20A: Mouse Fn1 contains three regions of AS. Cassette exons EDB (B), EDA (A), and the variable 3' splice site at the Variable (V) region that creates three different exons coding for 120, 95, or 0 extra amino acids. All together there are 12 possible isoforms of Fn1 when considering these three sites.

FIG. 20B: Ligamer pools targeting each site independently (B, A, V) and in combinations (BA, BV, AV, BAV) in were created and SeqZip was performed on Hepa1-6 RNA. Endpoint PCR of ligation products was performed and analyzed using native polyacrylamide gel electrophoresis (PAGE). The most abundant ligation product of each combination set ligation reaction is annotated.

FIG. 21 presents exemplary data using ten (10) representative mouse genes to assess intergene connectivity SeqZip analysis.

FIG. 22A: SeqZip ligation products can be analyzed using a paired-end (PE) read approach on the Illumina GE2 platform. Ligation products are sequenced from both ends of a single DNA molecule. Therefore, connectivity between the two previously distant RNA sequences (i.e., for example, purple exon 1 and green exon 2 above) is maintained when analyzing the SeqZip ligation product.

FIG. 22B: SeqZip was performed on pairs of exons in ten (10) genes from whole mouse brain RNA (See, FIG. 21). This panel demonstrates the isoforms expressed for the mouse AGRN gene. Isoform profiles were compared between traditional RT-PCR and SeqZip where the amplified ligation products run out on an electrophoresis gel (left). SeqZip ligation products were also analyzed using the Illumina PE approach (right). Clearly, the relative abundances of each of the four isoforms is very similar between RT-PCR and SeqZip on the gel, and the number of HTS tags mapping to specific AGRN SeqZip ligation products. Images from the gel represent cDNA or ligation products amplified with 40 cycles of PCR, run out on a 6% poly-acylamide gel, and stained with SybrGold®.

DETAILED DESCRIPTION OF THE INVENTION

Figures 1A, 1B, 1C:
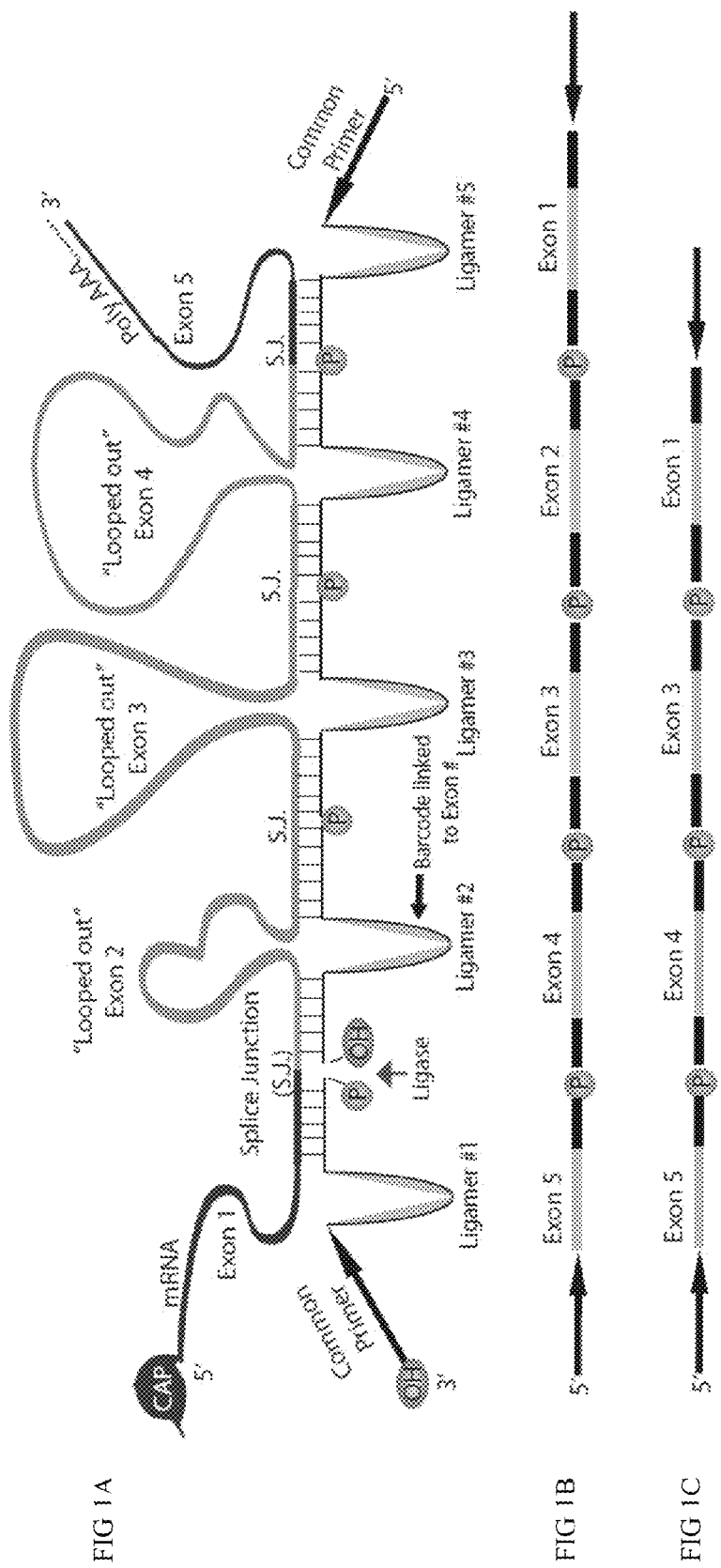
FIG. 1A: Five ligamers are shown, wherein each ligamer has at least one region of complementarity to a different exon on an mRNA strand, wherein splice junctions (S.J.) separate the different exon sequences. The central region of each ligamer comprises an exon-specific bar code (i.e., for example, ligamer #1 encodes a barcode specific for exon 1; ligamer #2 encodes a barcode for specific for exon 2 etc., see horizontal arrow). Exon-specific ligamers are designed to sequentially hybridize adjacent to one another at a predicted exon-exon junction (i.e., for example, ligamer #1 hybridizes adjacent to ligamer #2, wherein ligamer #2 also hybridizes adjacent to ligamer #3). Also shown are common 5' and 3' primer sequences attached to the first and last ligamers (i.e., ligamer #1 and ligamer #5). See, slanted arrows. Ligation may occur between the adjacent ligamers thereby joining their respective P— and OH— groups. See, vertical arrow.
FIG. 1B: One embodiment of a series of ligated ligamers to create a joined oligonucleotide maintaining exon 1-5 connectivity information.
FIG. 1C: One embodiment of a series of ligated ligamers to create a joined oligonucleotide demonstrating the presence of exons 1, 3, 4, 5 and the absence of exon 2.

The present invention is related to the field of genomics. For example, compositions and methods are described that are useful in determining intra- or intergene relationships such that physically distant exons may act in concert. Such exon coordination may be determined by using techniques that are capable of creating, ligating, and identifying oligonucleotides that reflect functional exon connectivity. These oligonucleotides comprise joined ligamers having a plurality of binding sites, wherein each binding site is complementary with a different exon.

In one embodiment, the present invention contemplates a method (e.g., SeqZip) that maintains the connectivity of mRNA exon sequences while reducing the overall effective mRNA transcript length, thereby providing compatibility with high-throughput sequencing platforms to read across multiple exon-exon junctions. In one embodiment, the method employs mRNA-templated DNA ligation of specific DNA oligonucleotide "ligamers" whose targeted sequences can be separated by hundreds or thousands of nucleotides. In one embodiment, each ligamer spans the ends of a single exon. In one embodiment, each ligamer spans the beginning and end of a large block of constitutively included RNA, thereby looping out an intervening sequence. In further embodiments, ligamers are aligned along a single mRNA molecule and then joined by enzymatic ligation. In one embodiment, each ligamer retains the identity of its corresponding RNA (i.e., for example, thereby preserving exon connectivity) while reducing the RNA length to ~40 nt.

Unfortunately, because most methods currently used for the large-scale analysis of isoform expression have distinct limitations and disadvantages, a complete picture of AS variant production is not yet available. For example, the prevalence of exon coordination relationships between different alternative splice (AS) regions separated by large spans of nucleotide sequence is not known. In one embodiment, the present invention contemplates an efficient, large-scale, single-molecule technique that maintains AS isoform sequence connectivity that provides exon coordination relationships between different AS regions.

I. Alternative Splicing

Soon after the discovery of introns, it was reasoned that genes could be (re)arranged in different combinations, greatly increasing the coding potential of a genome. Gilbert W., "Why genes in pieces?" *Nature* 271:501-501 (1978). The process of rearranging genes, now known as alternative splicing (AS), has proven to be an integral phase of gene expression in most eukaryotes. In just 15 years, the number of genes estimated to be alternatively spliced has grown incrementally: i) At first, approximately one of every twenty genes (~5%) were believed expressed by alternative pathways of RNA splicing in different cell types or growth states (Sharp P A., "Split genes and RNA splicing" *Cell* 77:805-815 (1994)); ii) Expressed Sequence Tag (EST) database searches increased that estimate to approximately 35%-59% (Modrek et al., "A genomic view of alternative splicing" *Nature Genetics* 30:13-19 2002)); iii) Soon after, analysis using specially designed microarrays resulted in an increased estimate of 74% (Johnson et al., "Genome-Wide Survey of Human Alternative Pre-mRNA Splicing with Exon Junction Microarrays" *Science* 302:2141-2144 (2003)); and iv) High-throughput sequencing (HTS) analysis of cDNA (referred to as RNA-Seq) has now demonstrated that between 86% and 95% of human multi-exon genes are subject to AS. Pan et al., "Deep surveying of alternative splicing complexity in the human transcriptome by high-throughput sequencing" *Nature Genetics* 40:1413-1415 (2008); Sultan et al., "A Global View of Gene Activity and Alternative Splicing by Deep Sequencing of the Human Transcriptome" *Science* 321:956-960 (2008); and Wang et al., "Alternative isoform regulation in human tissue transcriptomes" *Nature* 456:470-476 (2008).

AS is believed to play a role in the variety of gene expression (i.e., for example, human gene expression). AS appears to comprise a combinatorial nature that could potentially provide a physical explanation of evolutionary differences between the human and chimpanzee. Calarco et al.," Global analysis of alternative splicing differences between humans and chimpanzees" *Genes & Development* 21:2963-2975 (2007). Further, it is believed that AS variants may play a role in various diseases (i.e., for example, cancer). Tazi et al., "Alternative splicing and disease" *Biochimica et Biophysica Acta* 1792:14-26 (2009). Not only is it believed that almost all genes have alternatively spliced variants, but AS may often occur in a tissue-specific and/or a cell type-specific manner. Although it is not necessary to understand the mechanism of an invention, it is believed that AS provides insight into exon connections between comparably static genomic DNA sequence that are reflected by the highly flexible and adaptive abilities of organisms.

Alternative splicing has also been investigated on a 'single molecule' scale through hybridization of fluorescent probes. Zhu et al., "Single molecule profiling of alternative pre-mRNA splicing" *Science* 301:836-838 (2003). Recently, this approach has been expanded upon, and a proof of concept study combines regions of AS by 'looping out' intervening sequences has also been reported. Conze et al., "Single molecule analysis of combinatorial splicing" *Nucl Acid Res* gkq581-gkq581 (2010). Such probe studies are to be distinguished from the SeqZip methods discussed herein. First, SeqZip directly analyzes the RNA transcripts themselves and does not require cDNA synthesis. Also, because SeaZip directly sequencing ligation products the order of queried exons is maintained, unlike methods that hybridize fluorescent probes. Given the ability of SeqZip to measure multiple exons simultaneously, investigation of very complex alternative splicing events like those observed for KCNMA1 and DSCAM are contemplated herein. Nilsen et al., "Expansion of the eukaryotic proteome by alternative splicing" *Nature* 463"457-463 (2010); and FIG. 6.

A. Limitations of Current Large-Scale Methods

As with many areas of basic research, the field of AS relies on large-scale (i.e., for example, global, genome-wide, or high-throughput) techniques. Two currently available technologies employed for large-scale analysis of gene expression are microarrays and '2nd generation' HTS sequencing. Unfortunately, both of these techniques have fundamental limitations. For example, microarrays are limited by probe specificity and HTS sequencing is limited by read lengths.

Microarrays may rely on hybridization of a target sequence to a known probe averaging 25 to 100 nt in length. Southern E. M. "DNA microarrays. History and overview" *Methods in Molecular Biology* 170:1-15 (2001). Therefore, microarrays seem to indicate only the presence of short sequences in the target sample and may not provide adequate linkage information of these sequences. For example, a transcript known to display two different AS regions may be studied by using probes targeting these two regions. The two respective probes demonstrate an increase in signal to identify the occurrence of both AS events. Unfortunately, this approach cannot differentiate between an increase in transcripts containing only one AS region versus an increase in production of a single transcript containing both regions. Calarco et al., "Technologies for the global discovery and analysis of alternative splicing" *Advances in Experimental Medicine and Biology* 623:64-84 (2007). This binary analysis reflects the "exon connectivity problem." In addition to this disadvantage, microarrays also have problems associated with cross-hybridization, reproducibility, and a comparably small dynamic range. Such difficulties will likely hasten microarray displacement by RNA-Seq (HTS) as the preferred method for comprehensive analysis of gene expression. Shendure J., "The beginning of the end for microarrays?" *Nat Meth* 5:585-587 (2008).

Second generation HTS sequencing methodologies are currently being assessed for comprehensive transcriptome analysis. HTS has advantages over microarrays. Specifically, it allows de novo identification of AS isoforms over a larger dynamic range and may provide quantitative information. Mortazavi et al., "Mapping and quantifying mammalian transcriptomes by RNA-Seq" *Nat Meth* 5:621-628 (2008). Additionally, newly developed HTS techniques may enrich samples to examine low-abundance AS isoforms, making complete cataloging of AS events a possibility. Djebali et al., "Efficient targeted transcript discovery via array-based normalization of RACE libraries" Nat Meth 5:629-635 (2008); and Salehi-Ashtiani et al., "Isoform discovery by targeted cloning, 'deep-well' pooling and parallel sequencing" *Nature Methods* 5:597-600 (2008). Nonetheless, the current sequencing strategies (namely: chain termination, sequencing by synthesis, sequencing through hybridization and ligation, and pyrophosphate sequencing) and platforms ('Sanger,' Illumina, SOLiD, and 454, respectively) do not solve the exon connectivity problem without the advantages of some embodiments of the present invention. See, FIG. 2B.

Extended length single-molecule HTS read lengths have been reported, and other proposed approaches to solve the connectivity problem using single molecule techniques include traditional cloning, sequencing, or hybridization. Shendure et al., "Advanced sequencing technologies: methods and goals" *Nature Reviews Genetics* 5:335-344 (2004); Zhu et al., "Single molecule profiling of alternative pre-mRNA splicing" *Science* 301:836-838 (2003); Calarco et al., "Technologies for the global discovery and analysis of alternative splicing" *Advances in Experimental Medicine and Biology* 623:64-84 (2007); and Emerick et al., "Multivariate Analysis and Visualization of Splicing Correlations in Single-Gene Transcriptomes" *BMC Bioinformatics* 8:16-16 (2007). While these approaches can determine exon sequence connectivity, they scale poorly and are not feasible for large-scale applications.

II. The Exon Connectivity Problem

Solving the "exon connectivity problem," described above, has been an unmet need in the field of alternative splicing for some time. Black D. L., "Protein Diversity from Alternative Splicing: A Challenge for Bioinformatics and Post-Genome Biology" *Cell* 103:367-370 (2000). One possible solution to this problem might be direct high-throughput sequencing (HTS) of total cellular mRNA. Currently, HTS read lengths range between approximately 25 to 400 nucleotides (nt). Nonetheless, many believe that present technology requires a significant amount of time to allow for further development to obtain read lengths reaching many thousands of nucleotides that appear required for direct characterization of individual isoforms. Rothberg et al., "The development and impact of 454 sequencing" *Nat Biotech* 26:1117-1124 (2008); and Mortazavi et al., "Mapping and quantifying mammalian transcriptomes by RNA-Seq" *Nat Methods* 5:621-628 (2008).

Another limitation of current methods used to study alternative splicing is their inability to assess the relative abundance of AS isoforms. Knowing the relative abundance of individual AS isoforms is believed to allow for distinguishing background mRNA (i.e., for example, noisey splicing and/or carryover contamination) from functional alternatively spliced transcripts. It is further believed that individual AS isoform relative abundance information can identify specific AS isoforms associated with specific developmental or disease states. Dou et al., "Genomic splice-site analysis reveals frequent alternative splicing close to the dominant splice site" *RNA* 12:2047-2056 (2006); and Pan et al., "Quantitative microarray profiling provides evidence against widespread coupling of alternative splicing with nonsense-mediated mRNA decay to control gene expression" *Genes & Development* 20:153-158 (2006).

Further, a gene expression profile of cancer cells may identify cancer-specific AS isoforms, wherein the AS isoforms comprise diagnostic tools and/or therapeutic targets. Sazani et al., "Therapeutic potential of antisense oligonucleotides as modulators of alternative splicing" *The Journal of Clinical Investigation* 112:481-486 (2003); and Aartsma-Rus et al., "Antisense-mediated exon skipping: A versatile tool with therapeutic and research applications" *RNA* 13:1609-1624 (2007). In one embodiment, the present invention contemplates erroneous alternative splicing as causative factors in diseases and/or medical conditions including, but not limited to, cancer, spinal muscular atrophy, Hutchinson-Gilford Progeria syndrome, and multiple forms of familial dysautonomia. Tazi et al., "Alternative splicing and disease" *Biochimica et Biophysics Acta* 1792:14-26 (2009).

Other methods currently used to study isoforms include, but are not limited to, EST alignments, exon junction microarrays, RASL/DASL, BADGE, or LMF. Yang et al., "BADGE, Beads Array for the Detection of Gene Expression, a High-Throughput Diagnostic Bioassay" *Genome Res.* 11:1888-1898 (2001); Johnson et al., "Genome-Wide Survey of Human Alternative Pre-mRNA Splicing with Exon Junction Microarrays" *Science* 302:2141-2144 (2003); Peck et al., "A method for high-throughput gene expression signature analysis" *Genome Biology* 7, R61 (2006); Yeakley et al., "Profiling alternative splicing on fiber-optic arrays" *Nat Biotech* 20:353-358 (2002); Fan et al., "A Versatile Assay for High-Throughput Gene Expression Profiling on Universal Array Matrices" *Genome Research* 14:878-885 (2004); and Kim et al., "Bioinformatics Detection of Alternative Splicing" *Bioinformatics* 179-197 (2008).

Each of the above mentioned conventional methods has limitations. For example, EST alignment is hindered by cumbersome cloning and minimal sequencing lengths, consequently forcing a tedious piecing together of small reads into full length transcripts. Whether or not these transcripts represent true splice variants (i.e., are biologically functional), or merely represent artifactual byproducts of the splicing process, is difficult to determine. While such methods are reported to probe for exons at, or across, splice junctions such pairwise analysis cannot determine the connectivity of multiple exons within an individual mRNA (i.e., their sequential relationships cannot be verified). Rather, these methods provide a population average for each exon. Further, these methods also cannot determine whether alternative splicing events in one region of a transcript affect alternative splicing of a distal region, that is to say several kilobases distant, by determining changes in alternative exon choices. Ben-Dov et al., "Genome-wide Analysis of Alternative Pre-mRNA Splicing" *J. Biol. Chem.* 283:1229-1233 (2008).

A. Coordinated Distal Alternative Splice Issues

Current methods of identifying proximally-acting AS comprise a variety of biochemical methods coupled with HTS analysis. Unfortunately, no methods have been reported that are capable of identifying distally acting AS. In one embodiment, the present invention contemplates a method to identify long-range AS by determining intramolecular coordination between distal AS splices. For example, a schematic mRNA transcript is provided showing the relationships between coordinated distally acting AS regions. See, FIG. 2A. In this schematic, the 5' region of AS contains a cassette exon (yellow exon), which may or may not be included in the AS. This cassette exon is separated by many thousands of nucleotides from two mutually exclusive exons (i.e., for example, a blue exon or a red exon) that represent potential 3' AS regions. Although it is not necessary to understand the mechanism of an invention, it is believed that whether or not a cassette exon is included in an AS influences whether one, or both, of the mutually exclusive exons are also included in the AS. This type of AS regulation and control mechanism may represent a general and pervasive genomic phenomenon (i.e., for example, an inter- and intragene exon coordination phenomenon).

EST databases have also been examined demonstrating that approximately 25% of human genes contain multiple AS regions. An assessment as to how many of these AS regions could show exon coordinated effects have been attempted by using microarrays designed to report on inclusion levels of cassette exons in mammalian central nervous system tissues. These results produced a set of 38 pairs of exons mapping to the same gene that showed exon coordinated promotion or suppression of total AS exon inclusion. Such searches have generated a partial list of high-confidence exon coordinating AS regions that are separated by more than 1000 nt. See, Table 1.

gene families and splice variants. These speculative methods, however, were not detailed nor do they employ barcoded oligonucleotides or the ligation of adjacent oligonucleotides hybridized to an RNA template. Nilsson et al. "RNA-Templated DNA Ligation For Transcript Analysis" *Nucleic Acids Research* 29(2):578-581 (2001). Microarray-based approaches have also been suggested to profile alternative splicing of mRNA. Such methods are reported to be based upon an oligonucleotide ligation-dependent hybridization approach based on the RASL technique. Zheng et al., "A Database Designed To Computationally Aid An Experimental Approach To Alternative Splicing" *Pacific Symposium on Biocomputing* 9:78-88 (2004).

Figure 4A:
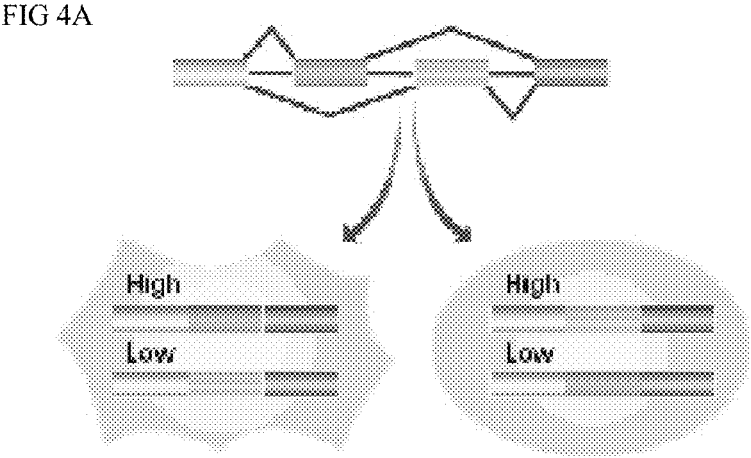
FIG. 4A: A pre-mRNA with mutually exclusive exons (green and yellow) is spliced in two ways (green-blue transcripts, yellow-blue transcripts). The pathway predominating in normal cells produces a high frequency of green-blue transcripts and can be distinguished from the pathway predominating in cancer cells that produces a high frequency of yellow-blue transcripts by measuring the use of the two splice junctions.
Figure 4B:
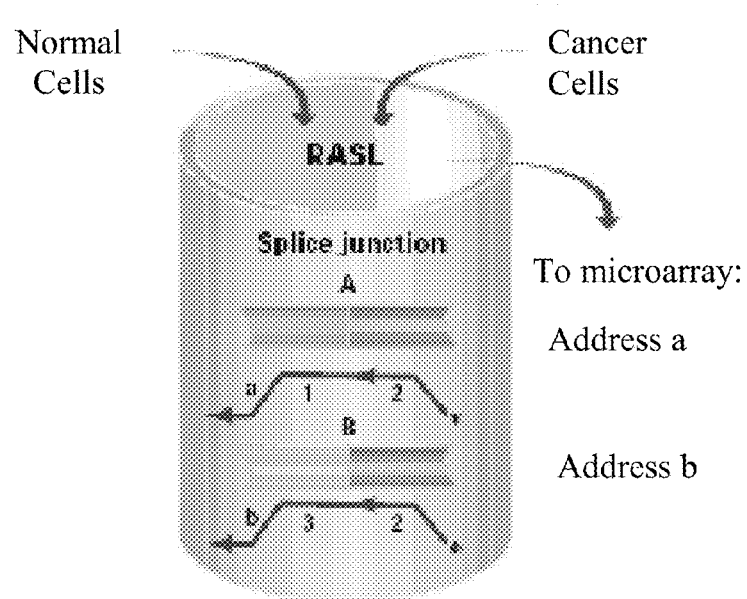
FIG. 4B: Illustrates a schematic of the RASL technique that measures splice junction use to determine the frequency of green-blue transcripts versus yellow-blue transcripts. From 1. Grabowski, P. Alternative splicing in parallel. Nat Biotechnol 20, 346-7 (2002).

Specifically, RASL (RNA-mediated selection, extension, and ligation) techniques rely on two oligonucleotides hybridizing adjacently on a single AS region. See, FIG. 4A. Total RNA from two cell types comprising a single AS region is generally the starting point for RASL analysis. Oligonucleotides complementary to exon sequences precisely flanking the single splice junction are then annealed to the mRNA. See, FIG. 4B. In normal cells, the predominant mRNA isoform (i.e., for example, green-blue isoform) serves as a template to juxtapose oligonucleotides 1 and 2, which are then ligated by T4 DNA ligase (splice junction A). Each ligated oligonucleotide contains T7 and T3 primer binding sites for controlled amplification by PCR. In cancer cells, the predominant splicing pattern (i.e., for example, yellow-blue iso-

TABLE 1

Mouse genes displaying exon coordinated AS events.

| Symbol | GeneName | Genetic Distance (nt) | Number of exons between AS exons | Length in nt of exons between |
|---|---|---|---|---|
| Chl1 | Cell adhesion molecule with homology to L1CAM (Chl1), mRNA | 154422 | 23 | 4665 |
| C330023M02Rik | RIKEN cDNA C330023M02 gene, mRNA (cDNA clone IMAGE: 4458590) | 22055 | 11 | 4089 |
| Prom1 | Prominin 1, mRNA (cDNA clone MGC: 25280 IMAGE: 4502359) | 43024 | 18 | 2533 |
| Vav2 | Vav2 oncogene (Vav2), mRNA | 118253 | 27 | 2140 |
| Dpp4 | Dipeptidylpeptidase 4, mRNA (cDNA clone MGC: 14076 IMAGE: 3982742) | 76886 | 22 | 2020 |
| Prom1 | Prominin 1, mRNA (cDNA clone MGC: 25280 IMAGE: 4502359) | 33054 | 15 | 1946 |
| Mdm1 | Transformed mouse 3T3 cell double minute 1 (Mdm1), transcript variant 2, mRNA | 23661 | 10 | 1845 |
| Ptprf | Protein tyrosine phosphatase, receptor type, F (Ptprf), mRNA | 9775 | 8 | 1633 |
| Pb1 | PREDICTED: *Mus musculus* RIKEN cDNA 2310032M22 gene (Pb1), mRNA | 33057 | 13 | 1556 |
| Cacna1c | Calcium channel, voltage-dependent, L type, alpha 1C subunit (Cacna1c), mRNA | 41498 | 11 | 1403 |
| C130076O07Rik | Neuronal cell adhesion molecule short isoform (Nrcam) mRNA, complete cds, alternatively | 11276 | 8 | 1227 |
| Neo1 | Neogenin (Neo1), mRNA | 17455 | 5 | 1112 |
| Ezh2 | Enhancer of zeste homolog 2 (*Drosophila*), mRNA (cDNA clone MGC: 5970 IMAGE: 3586689) | 14684 | 8 | 1030 |

(Fagnani et al., 2007).
Data sorted by length in nt of exons between probes of the same gene, then by Spearman correlation coefficient (not shown).

Unfortunately, this data, and other reported large-scale studies, preclude a complete determination of intramolecular AS coordination.

B. RASL/DASL mRNA-Templated Technologies

One report suggests that mRNA-templated ligation of DNA oligonucleotides might be used to efficiently detect single nucleotide variants of RNA sequences. This method was suggested to have a potential to provide direct analysis of RNA sequences, without PCR, to identify the relative abundance of specific mRNAs in cellular extracts, or include ligase-assisted probe ligation that might identify members of form) is detected by the ligation of oligonucleotides 3 and 2. Selection of poly(A)+ mRNA is accomplished by including a biotin-tagged oligonucleotide dT in the mixture of oligonucleotides applied in the annealing step, followed by transfer to streptavidin-coated tubes. One oligonucleotide of each ligated pair is designed with an arbitrary sequence (a or b) that specifies a particular address on the microarray. Hybridization of biotinylated oligonucleotides to the array is detected by measuring the fluorescence of labeled streptavidin. Ligation of RASL oligonucleotides are catalyzed with T4 DNA ligase. Ligated products are amplified using common primers and analyzed by hybridization of incorporated bar-coded regions to fiber-optic microarray. Grabowski, P., "Alternative splicing in parallel" *Nature Biotechnology* 20: 346-347 (2002).

The RASL approach differs in several aspects from some embodiments as disclosed herein. For example, the RASL method uses T4 DNA ligase. This enzyme is known to catalyze ligation of single-stranded DNA molecules and in a template-independent manner. Kuhn et al., "Template-independent ligation of single-stranded DNA by T4 DNA ligase" *The FEBS Journal* 272:5991-6000 (2005). In most embodiments, the present invention contemplates a method comprising multiple ligation events per template. Although it is not necessary to understand the mechanism of an invention, it is believed that T4 DNA ligase would confound results by introducing random ligated oligonucleotides between the common primers, thereby making an accurate determination of the original mRNA sequence difficult. Another disadvantage of RASL is that the oligonucleotides contain only a single region of complementarity to the template mRNA. This single complementary region limits RASL to determining the presence of short mRNA sequences. In one embodiment, the present invention contemplates a method for capturing looped out mRNA conformations using ligamers that bind to the mRNA in two distinct regions, thereby increasing query length. Finally, RASL relies on a single ligation event to create desired products. In one embodiment, the present invention contemplates a method comprising a plurality of ligations, thereby joining a plurality of ligamers into a single joined oligonucleotide.

For example, a RASL assay consists of the following five steps:
1) Annealing: Pooled oligonucleotides (complementary to specific mRNA splice junctions) and biotinylated oligo-dTs are mixed with isolated total cellular RNA.
2) Solid phase selection: The mix is transferred to a streptavidin coated PCR tube such that mRNAs (annealed to the oligo-dT and bearing specifically hybridized oligonucleotides) are immobilized.
3) RNA-mediated oligonucleotide ligation: Target oligonucleotides corresponding to juxtaposed (i.e. adjacent) splice junctions are ligated via T4 DNA ligase.
4) PCR amplification: Ligated products are amplified using universal primers on the ends of adjacently paired oligonucleotides.
5) Detection: The PCR products are detected (i.e. on a universal index array).

Nonetheless, oligonucleotides processed by this method are only complementary to a single splice junction donor and/or acceptor sequences—that is, these oligonucleotides do not comprise two regions of complementarity to the flanking regions of specific exons. Further, the RASL technique is disadvantageous because multiple ligation events to join a plurality of oligonucleotides hybridized to the same mRNA cannot be performed. Yeakley et al., "Profiling alternative splicing on fiber-optic arrays" *Nat Biotech* 20: 353-358 (2002). Consequently, in some embodiments, the present invention has specific advantages relative to previously known methods including, but not limited to, RASL. One advantage is that in the present invention mRNA exon connectivity information is maintained over long ranges of nucleotide sequences. Another advantage is that the present invention maintains AS isoform relative abundance during analysis that overcomes admitted limitations of the RASL technology.

For example, examination of the CD45 (PTPRC) gene expression reveals a limitation of the RASL assay. This receptor tyrosine phosphatase is known to play a critical role in T cell signaling. The gene is exclusively expressed in cells of hemopoietic lineage, which is consistent with its expression in both U-937 and Jurkat cells detected by both RT-PCR and RASL. Different isoforms can be easily distinguished by RT-PCR because of size differences. In contrast, the isoform variations were not evident by RASL (note that oligonucleotides were included in the assay for all potential combinations of alternative exons). The problem may be overcome in future experiments by using distinct sets of addressed (for alternative exons) and unaddressed (for common exons) oligonucleotides in different pools. Fan et al., "Nucleic Acid Detection Methods Using Universal Priming" U.S. Pat. No. 7,361,488 (herein incorporated by reference).

III. SeqZip Exon Connectivity Technology

In one embodiment, the present invention contemplates a method for establishing exon sequence connectivity. In one embodiment, the method comprises at least one alternatively spliced mRNA isoform from total cellular mRNA. Although it is not necessary to understand the mechanism of an invention, it is believed that the total cellular mRNA retains the relative transcript abundance information. Such a method provides an improvement over existing methods of mRNA isoform analysis that merely provide population averages and cannot determine the effect of splicing event(s) in one region of a transcript on distal splicing event(s) and/or assess the relative abundance of each isoform. Such disadvantageous existing methods include, but are not limited to, EST alignments (e.g., hindered by cloning and sequencing length and may produce artifacts), exon junction microarrays, RASL/DASL, BADGE, or LMF (e.g., which probe exons at or across splice junctions).

In one embodiment, the present invention contemplates a method for generating alternative mRNA splice sequences that maintains alternative transcript connectivity (i.e., for example, exon sequential order) and relative abundance (i.e., for example, repeat sequences). In brief, the method utilizes RNA-templated ligation of bar-coded oligodeoxynucleotides (i.e., for example, ligamers). In one embodiment, a ligamer comprises a 5' and a 3' sequence having complementary sequences relative to a corresponding 5' and 3' extremity of a specific mRNA exon. In one embodiment, the ligamer comprises a central region having an exon-specific bar code (i.e., for example, a unique, non-natural nucleic acid sequence that unambiguously identifies a single exon). In one embodiment, a plurality of ligamers are bound (i.e., for example, hybridized) to an mRNA such that at least two ligamers are aligned in tandem. In one embodiment, the at least two tandemly aligned ligamers are joined by ligation.

Although it is not necessary to understand the mechanism of an invention, it is believed that ligated ligamers may form a DNA molecule (i.e., for example, by PCR amplification) such that the recombinant DNA is shortened relative to the original mRNA exon-to-exon sequence and comprises complete exon connectivity information of the original mRNA. For example, when using ten (10) ligamers of thirty (30) nt each to ascertain connectivity between ten (10) exons, the length of the final ligated ligamer PCR amplification product is approximately 300 nt, as opposed to an original mRNA sequence of greater than fifteen hundred (1,500) nt. Such a three-fold reduction in sequence length results in a DNA sequence amenable to HTS.

One embodiment of the exon connectivity method described herein is illustrated using a simplified mRNA strand comprising five (5) exons. See, FIG. 1. The present invention contemplates, however, some embodiments involving complex mRNAs comprising hundreds, if not thousands, of exons such that exon connectivity may be determined on a genome-wide basis. For example, an mRNA may comprise five (5) exons, three (3) of which are alternatively spliced, thereby yielding eight (8) possible isoforms. See, FIG. 1A. To this mRNA, five unique ligamers are added, wherein ligamers #1 and #5 have regions on their 5' and 3' ends that are complementary to the 3' and 5' regions of Exons 1 and 5, respectively. In this example, ligamers #1 and #5 may also contain sequences that can later be used for PCR by function as primers.

Further, ligamers #2, #3, and #4 comprise at least two regions of complementarity to mRNA sequences residing in the flanking region(s) of a specific exon. In one embodiment, the flanking region-binding ligamer may comprise a central region comprising an exon-specific barcode sequence. The method may then allow the ligamers to hybridize to the mRNA on either side of the exon, therefore drawing together the terminal exon ends. This binding of the ligamer on either side of the exon forces the intervening exon region (i.e., the mRNA nucleotide sequence residing between the tandemly aligned ligamers) to "loop out" in order to maintain thermodynamic stability (i.e., for example, to maintain maximum entropy). After hybridization, one embodiment comprises ligating the 5' phosphorylated ends of a first ligamer to the 3' hydroxyl terminus of a tandemly aligned second ligamer. In comparison, the conventionally used RASL technique does not allow multiple ligation events to occur on the same template. Yeakley et al., "Profiling alternative splicing on fiber-optic arrays" *Nat Biotech* 20:353-358 (2002).

After ligation, the present invention contemplates a step wherein the original mRNA strand is degraded enzymatically, thereby leaving a series of joined ligamers that can be amplified by PCR to form a DNA product. See, FIG. 1B. In one embodiment, the present invention contemplates a DNA product composition comprising a series of joined DNA ligamers, wherein the DNA product comprises a nucleotide sequence directly corresponding to the original mRNA sequence. In one embodiment, the original mRNA sequence corresponds to the consecutive order of the ligamer barcodes. In one embodiment, the consecutive order of the ligamer barcodes maintains the exon connectivity of the original mRNA molecule.

In the simplified example shown in FIG. 1, the presence or absence of the middle three exons may be determined. See, FIG. 1B as compared to FIG. 1C. Although it is not necessary to understand the mechanism of an invention, it is believed that, under optimized conditions, all ligamer ligation products sharing the same common primers are amplified using a limited number of PCR cycles. It is further believed that the number of PCR cycles were chosen so as to stay within a linear range of amplification, thereby maintaining a constant relative abundance of each transcript within an RNA sample.

After PCR amplification of the series of joined ligation products into a DNA product, many technologies could potentially be used to analyze the data. For example, two such technologies are: i) hybridization to exon junction microarrays; or ii) PCR probing for specific ligation events. However, it is believed that HTS is capable of providing the most information. Although it is not necessary to understand the mechanism of an invention, it is believed that by using the DNA product (i.e., for example, the complete joined ligation sequence), HTS may provide information that uniquely identifies the mRNA, specifies exon connectivity, and identifies the number of times a given sequence is read thereby determining its abundance relative to other isoforms and other mRNAs.

Figure 15:
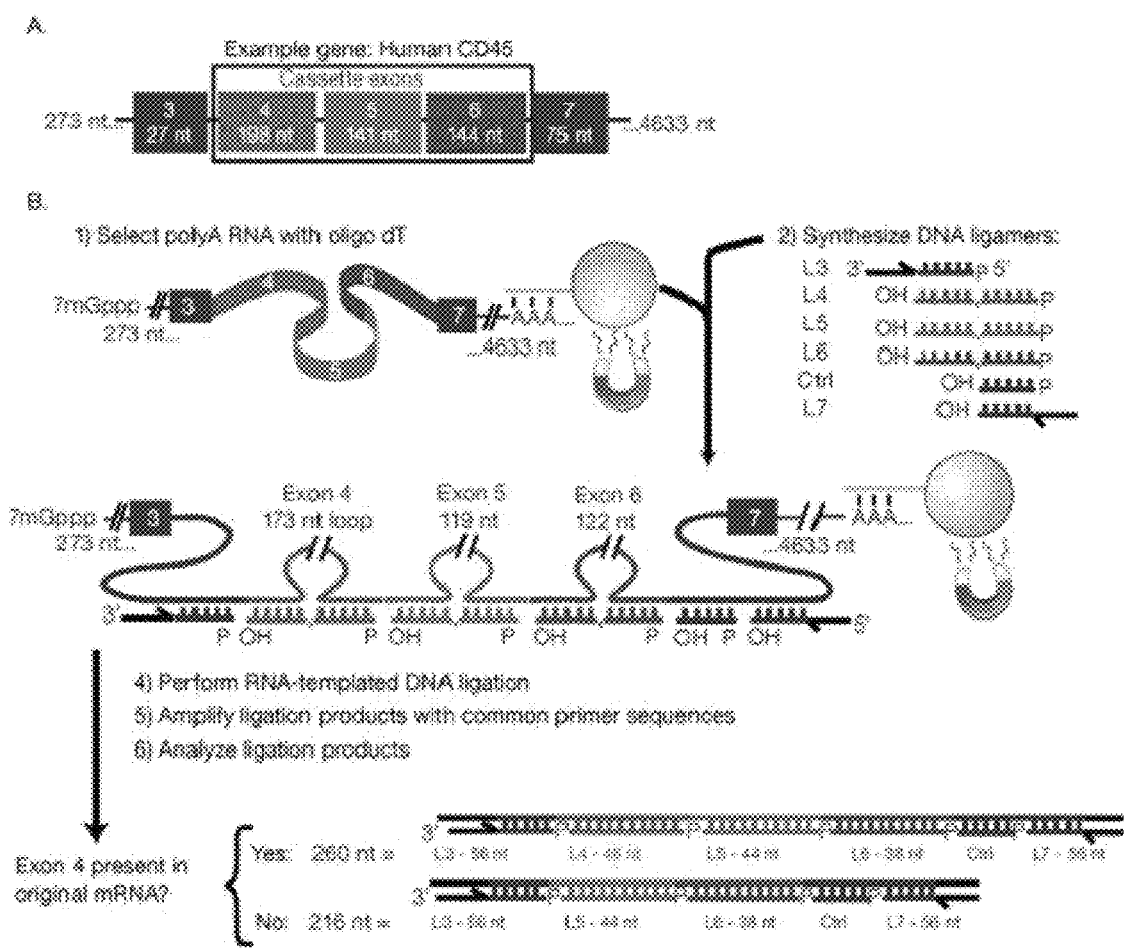
FIG. 15 illustrates one embodiment of an exon connectivity method (i.e., for example, SeqZip)

In one embodiment, the present invention contemplates a method (e.g., SeqZip) utilizing synthesized DNA ligamers' which hybridize to a specific sequence of RNA and are subsequently ligated together into an HTS-compatible read pair sequence. See, FIG. 15. (FIG. 1).

SeqZip differs significantly from previous reports investigating alternative splicing using ligation at splice junctions. Yeakley et al., "Profiling alternative splicing on fiber-optic arrays" *Nat Biotech* 20:353-358 (2002); and Fan et al., "A versatile assay for high-throughput gene expression profiling on universal array matricies" *Genome Research* 14:878-885 (2004). In one embodiment, the method relies on hybridization of the same DNA 'ligamer' to two different areas of the same RNA sequence. Although it is not necessary to understand the mechanism of an invention, it is believed that that is method allows for identifying to origin of multiple sequences contained within the same RNA transcript. These multiple sequences may originate for the same, or different genes. In one embodiment, because SeqZip relies on mRNA templated DNA ligation, it does not require the conversion of RNA to cDNA using Reverse Transcriptase followed by Polymerase Chain Reaction (i.e., RT-PCR). In one embodiment, the method provides multiple ligation events that are used to capture multiple areas of sequence variability. These and other features of SeqZip demonstrates the origin of multiple sequences that are contained in the same RNA sequence.

A mouse gene model (Fn1) was used to test a previously proposed influence of EDA exon choice on subsequent splicing of the IIICS exons. Fededa et al., "A polar mechanism coordinates different regions of alternative splicing within a single gene" *Molecular Cell* 19:393-404 (2005); and Chauhan et al., "Alternative splicing of fibronectin: a mouse model demonstrates the identity of in vitro and in vivo systems and the processing autonomy of regulated exons in adult mice" *Gene* 324:55-63 (2004). These previous reports suggested interactions between these two exonic regions that are separated by ~6 kbp in the genomic sequence (~815 nt in the mRNA), a region that encodes six (6) constitutively included exons. In contrast, the data presented herein indicate that the respective percent inclusions of the EDA exon and IIICS exonic region are the same when these exons are analyzed individually or together (infra). The data also contradicts other reports by suggesting that there is little or no influence of the 5' EDA exon on subsequent splicing decisions at the 3' IIICS exonic region. The data presented herein demonstrates that unique AS isoforms can serve as templates for the ligation of synthesized DNA ligamers designed to compress AS isoform sequence information into short nucleotides products that are compatible with HTS sequencing techniques. The method was optimized by using an art-accepted alternative splicing model comprising a human T-cell line. Such optimization may result in an accurate and reproducible identification of single gene local AS patterns, but can also assay more complex forms of AS.

A. Ligamer-RNA Hybridization

In one embodiment, the present invention contemplates a composition comprising an RNA-templated ligation of a barcoded oligodeoxynucleotide (i.e., for example, a ligamer). In one embodiment, the ligamer comprises a 5' and 3' sequence complementary to the corresponding 5' and 3' extremities of a specific exon with a unique central region containing an exon-specific bar-code. Although it is not necessary to understand the mechanism of an invention, it is believed that ligamers at the ends of each transcript may contain sequences that can be used for common PCR primers. In one embodiment, the ligamer comprises an internal ligamer, wherein the internal ligamer comprising at least two regions of complementarity to flanking regions of a specific exon. In one embodiment, the ligamer—oligonucleotide isoform complex is formed, wherein more than one ligamer may align in tandem, thereby resulting in a "looping out" of intervening mRNA regions. In one embodiment, the complex is ligated by joining the 5' and 3' ends of adjacent ligamers. In one embodiment, the mRNA complex is subjected to enzymatic degradation thereby leaving a plurality of joined DNA ligamers. In one embodiment, at least one joined DNA ligamer comprises a sequence directly corresponding to the mRNA from which it was created. Although it is not necessary to understand the mechanism of an invention, it is believed that the joined DNA ligamer sequence reflects the exon connectivity of the single mRNA molecule from which it was derived. It is further believed that, the resulting DNA molecule reduces the sequence of the mRNA exons into a much shorter length that is more amenable to sequence and abundance analysis.

A series of representative ligamers compatible with the present invention are disclosed herein. See, Table 2.

TABLE 2

Representative Ligamer Sequences

| | Target Gene | Ligamer Name | Sequence | Notes |
|---|---|---|---|---|
| FN1-5.0 | Mouse Fibronectin | CR-FN1-EDB-E24 Term | /5Phos/ATA GGG GCA CTT TCC TTG TCT GAG CGG GCT GGC AAG GC (SEQ ID NO: 1) | Adjacent to E24 Ctrl lig-has appropriate sequence + 454 Forward primer sequence |
| | Mouse Fibronectin | CR-FN1-EDB-E24 Ctrl Lig | /5Phos/CTG GGA CAA CGG TAT CAG AG (SEQ ID NO: 2) | Targets Mouse EDB (exon 25)-Complementary to 3' most mRNA sequence of exon 24-allows separation of EDB(-) events from NTL |
| | Mouse Fibronectin | CR-FN1-EDB-Ligamer 5.0 | /5Phos/CCG TTT GCT GTG TCA GTG TCA TCA AGT GAG CTG GGG CAC CT (SEQ ID NO: 3) | Loops out Mouse FN1 exon 25 (EDB) |
| | Mouse Fibronectin | CR-FN1-EDB-E26 Term Lig | GCC TCC CTC GCG CCA TCA GAC CGT GGG AGG AGG GAC AG (SEQ ID NO: 4) | Complementary to 5' most sequence of Exon 26 + 454 Reverse primers sequence |
| | Mouse Fibronectin | CR-FN1-EDB-EDA Span (E26-32) | /5Phos/TGG TCA CTG CAG TTT GAA CCT CAT CAC CGT GGG AGG AGG GAC AG (SEQ ID NO: 5) | Loops out from Mouse FN1-exons 26 to 32 (hooks up EDB + EDA) |
| Mouse FN1 V3.0 & Ctrl Lig 4.0 | Mouse Fibronectin | CR-FN1-V3.0-Exon32 | /5Phos/TGG TCA CTG CAG TTT GAA CCA TCA TCA TCT GAG CGG GCT GGC AAG GC (SEQ ID NO: 6) | Exon 32 + AS Primer sequence |
| | Mouse Fibronectin | CR-FN1-V3.0-Exon33(EDA) | /5Phos/CTG TGG ACT GGA TTC CAA TCA TCA TCA CAG TCC TTT AGG GCG ATC AAT GT (SEQ ID NO: 7) | Exon 33 |
| | Mouse Fibronectin | CR-FN1-V3.0-Exon34-39 | /5Phos/CTG TCT TCT TCC TCC CAA TCA GGG TCA TCA GGG CGC AGG AAT GG (SEQ ID NO: 8) | Exon 34-39-loops out 813 nt between |
| | Mouse Fibronectin | CR-FN1-V3.0-Exon40a(120) | /5Phos/CTG TGG AGG GAA CAT CTC ATC ACA GTT GGG GAA GCT CAT (SEQ ID NO: 9) | Exon 40 |
| | Mouse Fibronectin | CR-FN1-V3.0-Exon40(95) | /5Phos/CTG TAG AGG CAT TTG GAT TGA GGT CAT CAG TGA TGA AGG GGG TCT TTT GAA (SEQ ID NO: 10) | Exon 40a' |
| | Mouse Fibronectin | CR-FN1-V3.0-Exon40A'(0) | GCC TCC CTC GCG CCA TCA GAT CAT CAG AGA GAG AGC TTC CTG TC (SEQ ID NO: 11) | Sense Primer + Exon 40A' |
| | Mouse Fibronectin | CR-FN1-V Region Lig Control 4. | /5Phos/CTG TCT TCT TCC TCC CAA TCA GGG (SEQ ID NO: 12) | Allows separating NTL from (0)-Targets 3' most sequence of exon 39 |
| | Mouse Fibronectin | CR-FN1-V Region-Term-4.0 | /5Phos/GCT CAC TCT TCT GAT TGT TCT TCA GGG TCA TCA TCT GAG CGG GCT GGC AAG GC (SEQ ID NO: 13) | Sense Primer + 5' sequence adjacent to V region ctrl 4.0 ligamer sequence |
| | Mouse Fibronectin | CR-FN1-EDA Lig Control 4.0 | /5Phos/TGG GCG CAG GAA TGG (SEQ ID NO: 14) | Allows separating NTL from (EDA)-Targets 5' most sequence of exon 34 |
| | Mouse Fibronectin | CR-FN1-EDA-Term-4.0 | GCC TCC CTC GCG CCA TCA GAT CAT CAT GTC ACC TGA CTG AAC TTC AGA TTG G (SEQ ID NO: 15) | Sense Primer + 3' sequence adjacent to V region ctrl 4.0 ligamer sequence |
| Translig V1.0 | Mouse Fibronectin | CR-TransLig-FN1-Exon34-3' | GCC TCC CTC GCG CCA TCA GAC ATG AGT CCT GAC ACA ATC AC (SEQ ID NO: 16) | Sense primer sequence + FN1 Exon 34-3' most sequence |
| | Mouse Fibronectin 3' and Mouse RPL15 5' | CR-Translig-FN1(35-2)RPL14 | /5Phos/CAC TGA CTT CGT ATT TAG TGG CCA CTC ATC ACC TGT TCT GAT CAA TGA CAT CTA CAA (SEQ ID NO: 17) | 3' end contains sequence targeting 5' most sequence of FN1 exon 35 and 5' end contains 3' sequence of RPL15 exon 2 |
| | Mouse RPL15 | CR-Translig-RPL14-Exon3 | /5Phos/GGT CCA TCC ACT AAA GCT CTG AGC GGG CTG GCA AGG C (SEQ ID NO: 18) | RPL15 5' sequence of exon 3 followed by antisense primer sequence |

TABLE 2-continued

Representative Ligamer Sequences

| Target Gene | Ligamer Name | Sequence | Notes |
|---|---|---|---|
| Cd45 Endog | Human CD45 | CR-CD45-E7-454-Endog | GCC TCC CTC GCG CCA TCA GAT CGT AGG CAC CTG AAA GGG CTC AGA GTG GTT GTT TC (SEQ ID NO: 19) | Sense Primer sequence + 5' sequence of exon 7 adjacent to R0Ctrl Lig |
| | Human CD45 | CR-CD45-E7-R0-Ctrl | /5Phos/AGA GGC ATT AAG GTA GGC AT (SEQ ID NO: 20) | Allows separation of R0 from NT1 events-targets 3' most sequence of Exon 7 |
| | Human CD45 | CR-CD45-E6-454-Endog | /5Phos/CTG AGG TGT TCG CTG TCA TCA CCT CTC TCC TGG GAC AT (SEQ ID NO: 21) | Exon 6 |
| | Human CD45 | CR-CD45-E5-454-Endog | /5Phos/CTG AGA TAG CAT TGC TGC TCA TCA CGT CTG TAC TGA TGA AAC AC (SEQ ID NO: 22) | Exon 5 |
| | Human CD45 | CR-CD45-E4-454-Endog | /5Phos/CTG TGG TAT TAA AAG CAC TAT CAT CAC ATC TTT GCT GTA GTC AAT C (SEQ ID NO: 23) | Exon 4 |
| | Human CD45 | CR-CD45-E3-454-Endog | /5Phos/CAG TGG GGG AAG GTG TTG GGC TGT AGG CAC CAT CAA TCT GAG CGG GCT GGC AAG GC (SEQ ID NO: 24) | Exon3 + Antisense primer sequence |

All exon notations according to ExonMine ®.
(DB loops out Mouse FN1 exon 25.

Figure 9:
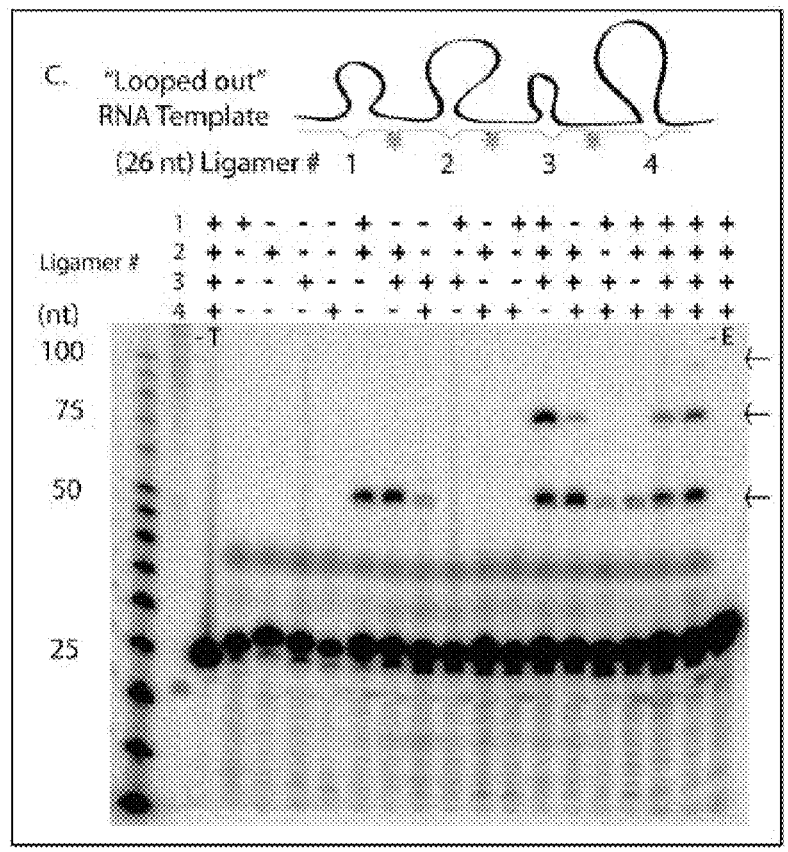
FIG. 9 presents exemplary PAGE data demonstrating the "looping out" phenomenon by ligating various combinations of ligamer pairs. '−T' refers to no template in the reaction, '−E' refers to no enzyme in reaction.

In one embodiment, the present invention contemplates a method wherein intervening regions between the ligamer pairs "loop out" an mRNA template. To examine this process, a set of four (4) ligamers were synthesized wherein each ligamer comprises two regions of complementarity to the mRNA. For example, these complementary regions may be separated by approximately 9 to 78 nt of transcript sequence. Various combinations of ligamer pairs were incubated with the same RNA template and enzyme according to the shown matrix. See, FIG. 9. Ligation products were only observed when adjacent ligamers were present in the reaction. Using these $^{32}$P labeled ligamers, the data demonstrate that these ligamers can capture the template in a "looped out" conformation, and that RNL2 will only catalyze ligation of adjacent ligamers under these constraints.

B. Ligamer Ligation

Currently used ligation-based alternative splicing methods rely on T4 DNA ligase to join DNA oligos. Unfortunately, T4 DNA ligase is quite promiscuous in terms of substrate specificity, and will perform blunt ligation (i.e., for example, non-templated ligation (NTL)). Kuhn et al., "Template-independent ligation of single-stranded DNA by T4 DNA ligase" *The FEBS Journal* 272:5991-6000 (2005). The data presented herein demonstrates an empirical process that screened commercially available double stranded ligases to identify ligases that would perform RNA-templated DNA ligation with little or no NTL.

Figure 2:
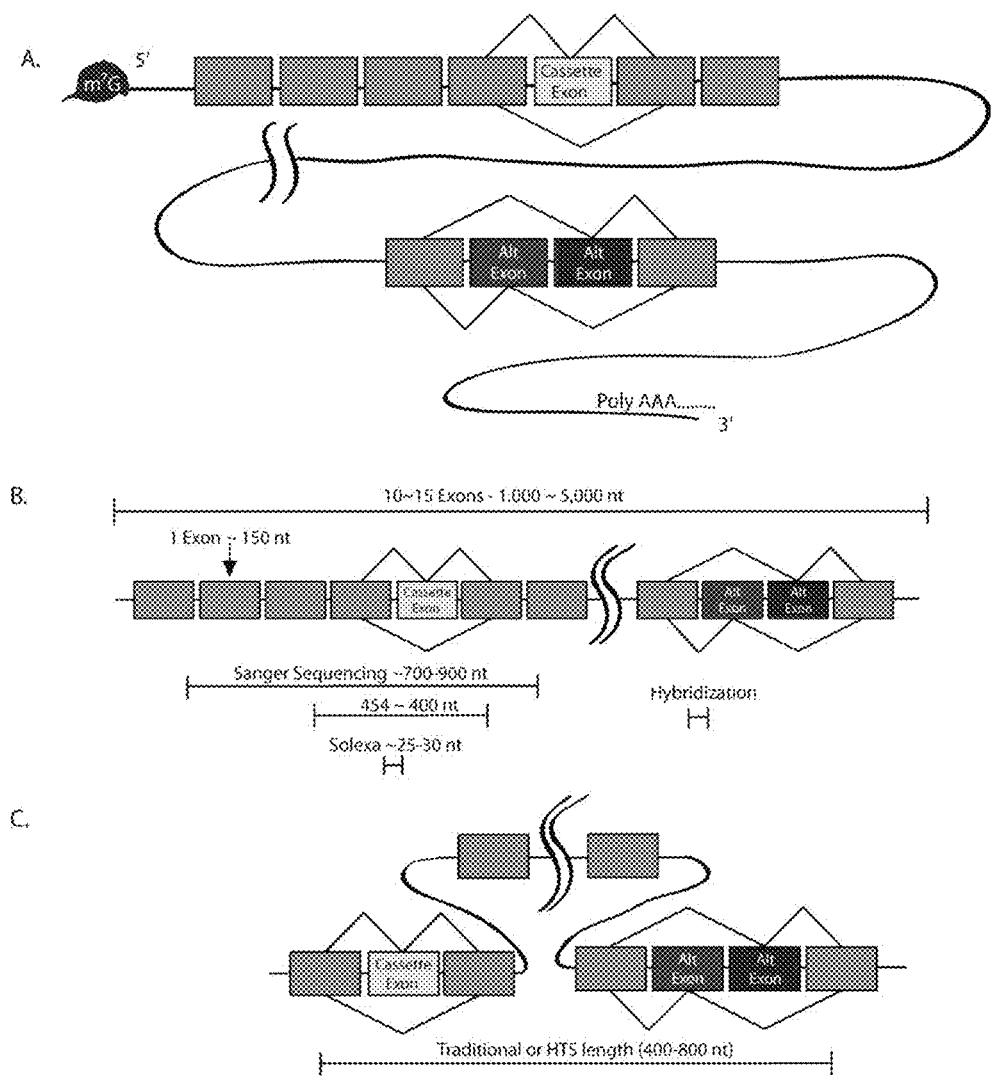
FIG. 2 illustrates how one embodiment of the present invention overcomes one limitation of investigating distal coordinated AS regions using conventional methods
Figure 16:
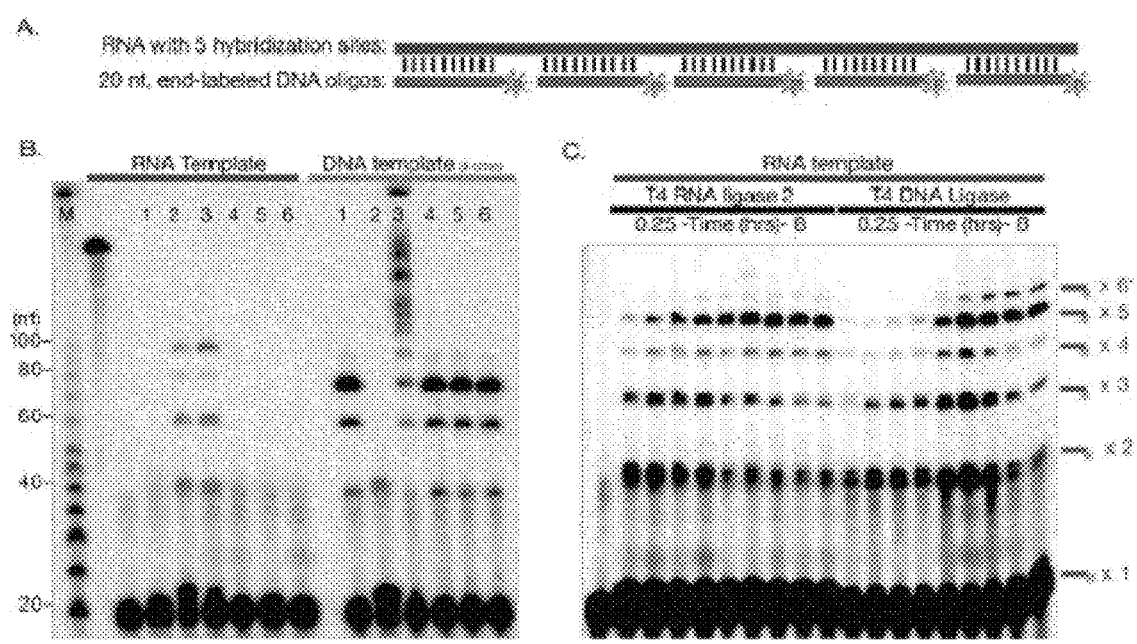
FIG. 16 presents exemplary data showing improved RNA-templated DNA ligation using Rnl2 ligase as compared to T4 DNA ligase.

Using in vitro transcribed RNA and end-labeled oligos, it was determined that along with T4 DNA ligase, T4 RNA Ligase 2 (Rnl2) will also catalyze RNA-templated DNA ligation. See, FIGS. 16A and 16B. (FIG. 2, panels A&B). Rnl2 ligase has not been previously reported to catalyze multiple RNA-templated DNA-DNA ligation events on a single template. The data demonstrate that Rnl2 ligase does catalyze a significantly lower level of NTL as compared to T4 DNA ligase. See, FIG. 16C. (FIG. 2, panel C). Another significant advantage of Rnl2 ligase over T4 DNA ligase is that Rnl2 ligase does not perform DNA template DNA-DNA ligation, providing a useful feature against DNA contamination in sample preparations. See, FIG. 16A. (FIG. 2, panel A).

T4 DNA ligase has been reported to catalyze an RNA-templated DNA-ligation event. Nilsson et al., "RNA-templated DNA ligation for transcript analysis" *Nucl Acids Res* 29:578-581 (2001); and Yeakley et al., "Profiling alternative splicing on fiber-optic arrays" *Nat Biotech* 20:353-358 (2002). However, T4 DNA ligase is also known to efficiently catalyze template-independent, blunt-end ligation. Kuhn et al., "Template-independent ligation of single-stranded DNA by T4 DNA ligase" The FEBS Journal 272:5991-6000 (2005). Consequently, T4 DNA ligase is not useful for the presently contemplated invention because this ligase would result in significant contamination thereby preventing identification of efficient ligation of multiple oligonucleotides on an RNA template (i.e., for example, mRNA). Other ligases including, but not limited to, thermostable and NADH-dependent varieties may also be useful for selective RNA-templated DNA-ligase activity.

To assess the functionality of various ligase enzymes, a set of oligonucleotides (herein called "ligamers") were created that were complementary to a linear region of a template RNA. Ligamers were end-labeled using $^{32}$P. See, FIG. 7, bottom panel. Template RNA was then in vitro transcribed and incubated with the set of ligamers, a particular ligase, and the appropriate buffer. Reactions were allowed to proceed at the manufacturer's recommended temperature for 1 hour. The template RNA was then digested with RNase, and ligated samples were separated using denaturing polyacrylamide gel electrophoresis (PAGE). Both T4 DNA ligase and T4 RNA ligase II (herein, RNL2) showed partial and complete (4-way) ligation products. See, FIG. 7. In all, a panel of six different ligases was screened for RNA-templated DNA ligation activity. Numbers refers to lane annotation on the PAGE gel as follows:
2—*E. Coli* DNA Ligase,
3—T4 DNA Ligase,
4—RNL2,
5—Thermo DNA ligase,
6—Tsc DNA Ligase, and
7—Tth DNA ligase.
Lane 8 contains T4 DNA ligase and a DNA version of the template. B—Blank, and T—Template RNA transcribed with 32P UTP. M—End-labeled 5 bp ladder (after 50 nt, shifts to 10 nt ladder). Samples were allowed to react for 1 hr at the manufacturer's specified temperature. After incubation, samples were treated with RNase, mixed 1:1 with formamide loading buffer and run on a denaturing PAGE gel.

Figure 8:
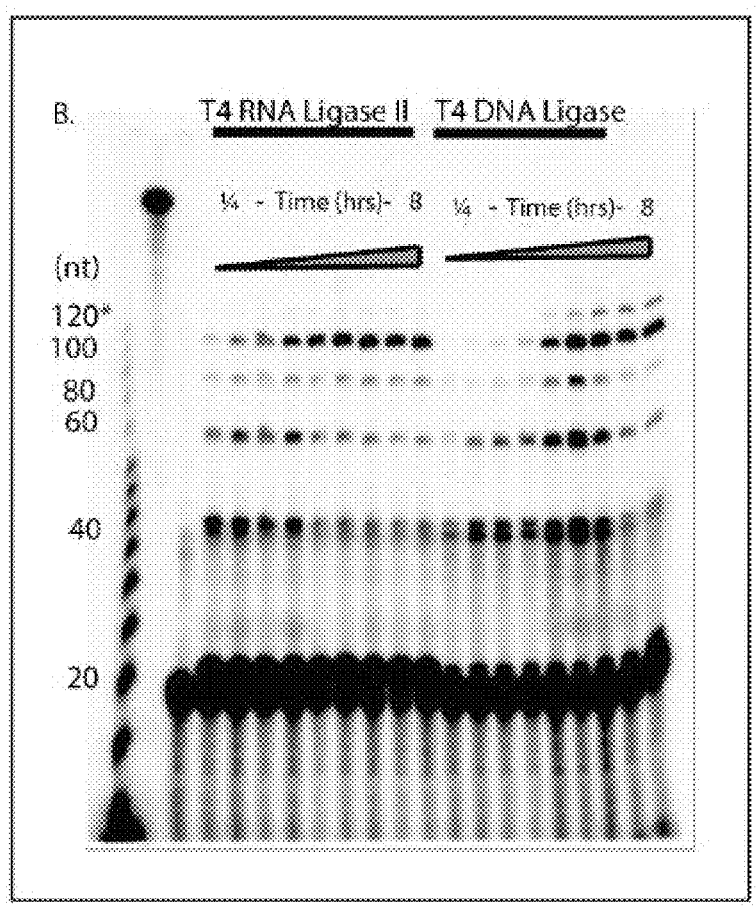
FIG. 8 presents exemplary PAGE data comparing a ligation time course comparing T4 DNA ligase to T4 RNA ligase II.

A ligation time-course was then performed comparing T4 DNA ligase and RNL2. The ligation reactions were terminated after ¼, ½, ¾, 1, 2, 3, 4, and 8 hrs (2 samples for 8 hr timepoint). Both enzymes show 100 nt product between ¾ and 8 hrs. The data demonstrate products of T4 DNA ligase's blunt ligation activity after just 3 hours (i.e., for example, the 120* product). In contrast, RNL2 produced desired length ligation products after just 1 hour and with significantly less blunt ligation out to 8 hours. See, FIG. 8. These data demonstrate that RNL2 more efficiently ligates multiple oligonucleotides as compared to T2 DNA ligase.

Under optimized conditions, it is believed that all ligation products sharing a common primer may be amplified using a limited number of PCR cycles such that amplification remains in the linear range, thereby maintaining the relative abundance of each transcript. Numerous technologies may be used to detect a barcoded signal after PCR. These include, but not limited to, hybridization to exon junction microarrays, PCR probing for specific ligation events, or HTS. For example, direct analysis of the DNA sequence via HTS can uniquely identify the mRNA and its exon connectivity, while the number of times a given sequence is read would report its abundance relative to other isoforms and other mRNAs.

In one embodiment, the present invention contemplates an RNA-templated DNA ligation method (i.e., for example, SeqZip) using Rnl2 ligase that provides a useful tool to investigate RNA biology. In one embodiment, Rnl2 ligation may be useful in determining whether a cell actually transcribe all 180 kb of intron 44 (e.g., the Xp21 locus) in human dystrophin. In one embodiment, RNL2 ligation may be useful in determining whether piRNAs are transcribed as huge clusters of 10K or more and subsequently processed. These questions are now experimentally addressable using SeqZip.

C. SeqZip Ligation Products

Figure 10:
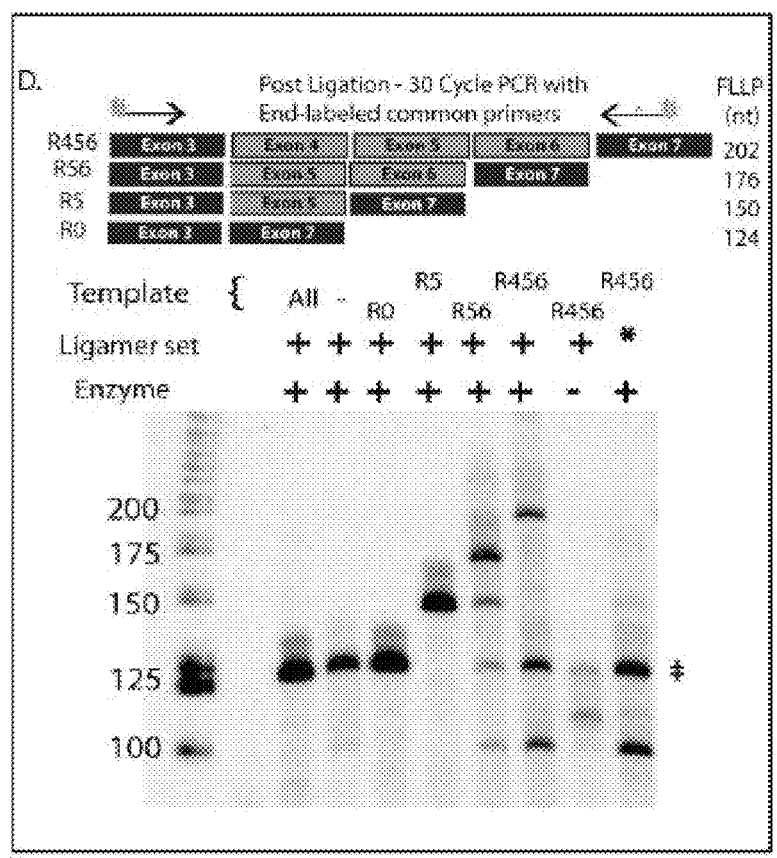
FIG. 10 presents exemplary PAGE data demonstrating the isolation of a joined ligation product for sequencing. '*' refers to a set of ligamers lacking a ligamer targeted to the variable exon 5. FLLP=Full Length Ligation Products, whose length is measured as nucleotides (nt). '‡' refers to either a product of non-templated ligation of terminal ligamers, or a PCR dependant species.

In one embodiment, the present invention contemplates a method comprising producing an appropriate ligation product length. In one embodiment, the ligation products were produced from a set of ligamers in a template-dependent fashion. For example, ligamers designed to probe the presence of the three alternatively spliced exons of the human CD45 gene were synthesized. The results show a template dependence of full-length ligation products (FLLPs) from the same set of ligamers. Specifically, different AS isoforms of the human CD45 gene were in vitro transcribed. These isoforms contain different combinations of exons 4, 5, and 6. These isoforms are referred to as R456, R56, R5, and R0, according to the presence of the alternatively spliced exons (shown in green). A set of ligamers capable of capturing the mRNA in a looped out conformation were allowed to react with different AS isoforms. After ligation, products were amplified with 30 PCR cycles using end-labeled common primers. PCR samples were mixed with denaturing LB and analyzed using PAGE. Sequencing confirms that the 202, 176, 150, and 134 nt bands contain full or partial sequences, respectively, corresponding to the common primers. See, FIG. 10.

The utility of SeqZip in the measurement of endogenous mRNA isoforms was validated by comparing ligation product abundances to those obtained from traditional reverse transcriptase (RT) methods. The model gene chosen for development efforts was human CD45. CD45 has been heavily studied and has revealed many aspects of alternative splicing regulation. Lynch, K. W. "Consequences of regulated pre-mRNA splicing in the immune system" *Nat Rev Immunol* 4:931-940 (2004). This gene also presents a relatively simple isoform profile through alternative inclusion of three cassette exons. See, FIG. 15A. (FIG. 1, panel A).

Figure 17:
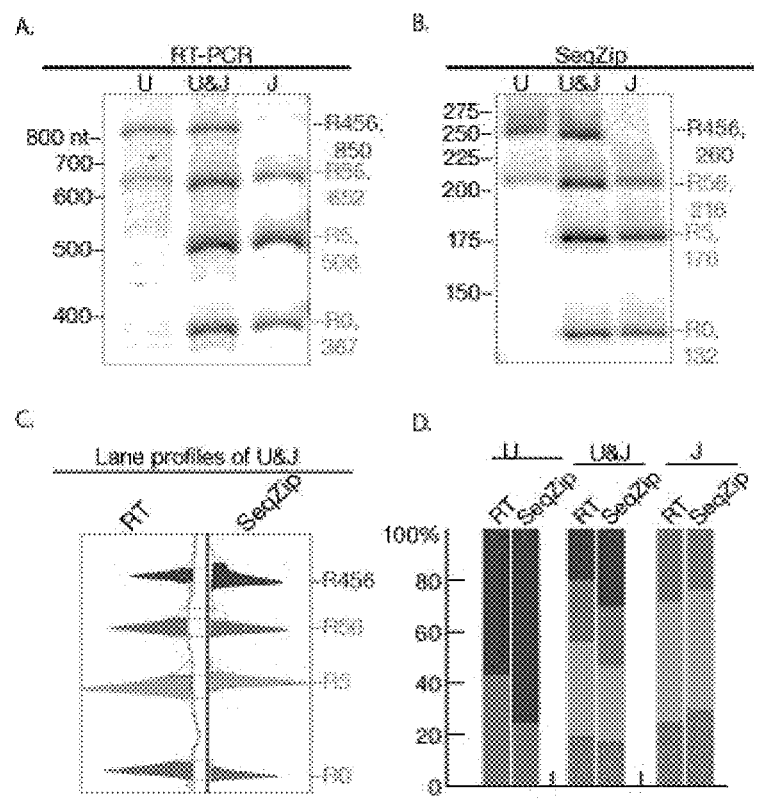
FIG. 17 presents exemplary data comparing SeqZip exon connectivity to Reverse Transcriptase Polymerase Chain Reaction (RT-PCR) exon connectivity using a CD45 gene model.

PolyA was selected RNA from two different human T-cell lines (U-937 and Jurkat) and analyzed for CD45 isoforms using RT-PCR and SeqZip. As expected, RT-PCR shows that the two cell lines expressed different isoform profiles of CD45. See, FIG. 17A. (FIG. 4, panel A). Compared to RT-PCR, SeqZip reports a very similar profile for both cell types (FIG. 4, panel B) and integration of each band shows that RT-PCR and SeqZip agree in relative CD45 isoform expression. See, FIGS. 17B and 17D, respectively. (FIG. 4, panel D). Any bias imparted by the number of required ligation events for the production of a specific full-templated ligation event (FTL) would be apparent when comparing the U-937 and Jurkat expression of the longest isoform (i.e., for example, R456). FTLs from this isoform require four ligation events and if this requirement skewed results in terms of relative quantity to those mRNAs requiring fewer ligations, the apparent abundance of R456 in the U-937 cell line would not be so comparable between RT-PCR and SeqZip. These data demonstrate that SeqZip can be used to investigate endogenously expressed isoforms, and support a direct comparison of expression profiles obtained using SeqZip to those using conventional RT-PCR.

D. Trans-RNA Transcript Hybridization And Ligation

Trans-RNA transcript hybridization and ligation was investigated because as longer sections of RNA are 'looped out', a single ligamer may hybridize to different transcripts (e.g., trans-transcript hybridization) followed by ligation into a single FTL. Although it is not necessary to understand the mechanism of an invention, it is believed that if a single ligamer hybridizes simultaneously to two different mRNAs, the resulting FTL event would not accurately report on the sequence content of the original message. Additionally, the ability to analyze coordination of sequences would be compromised.

Figure 3:
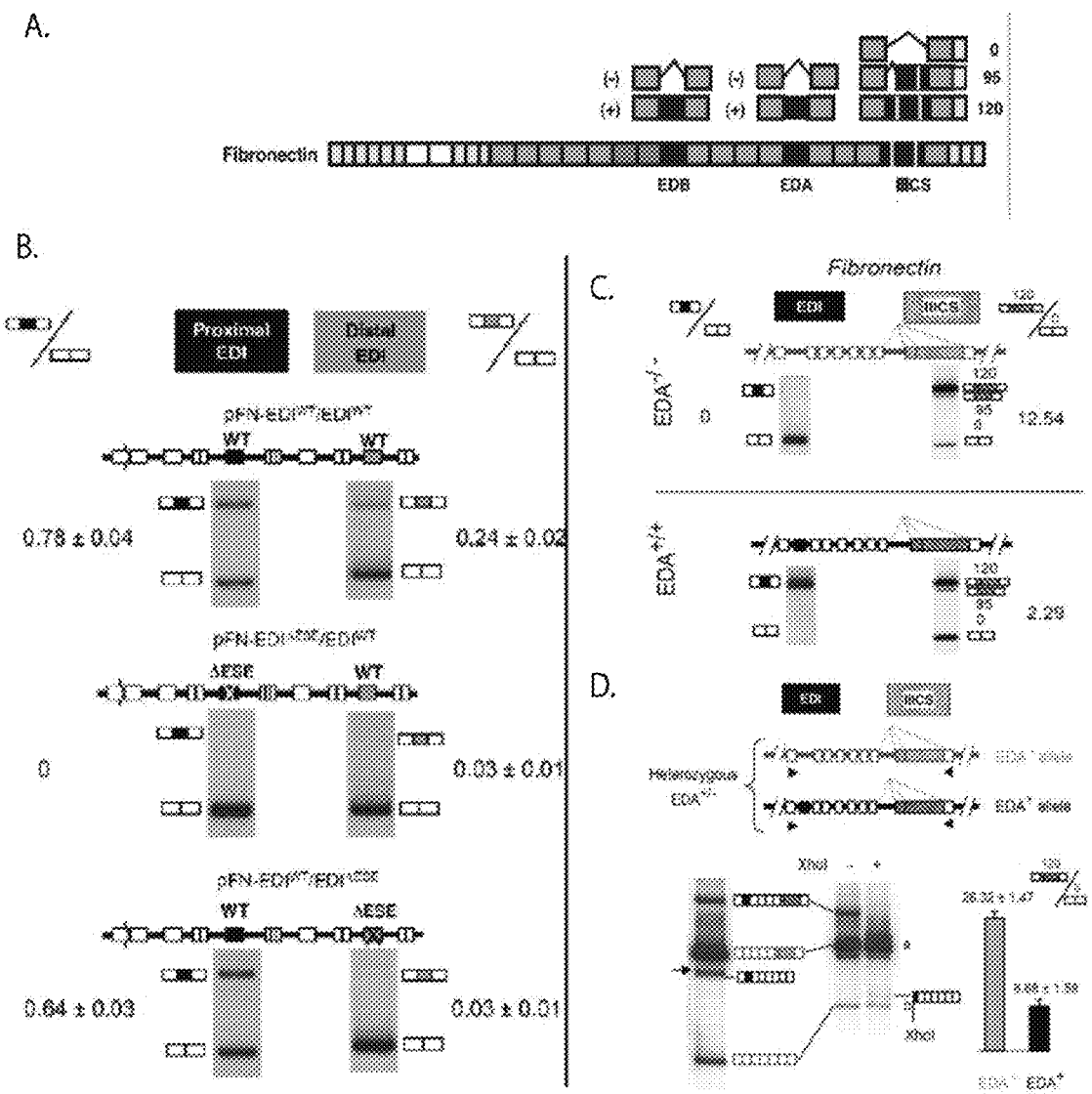
FIG. 3 presents a representative demonstration of coordinated AS regions in mouse fibronectin.
Figure 18:
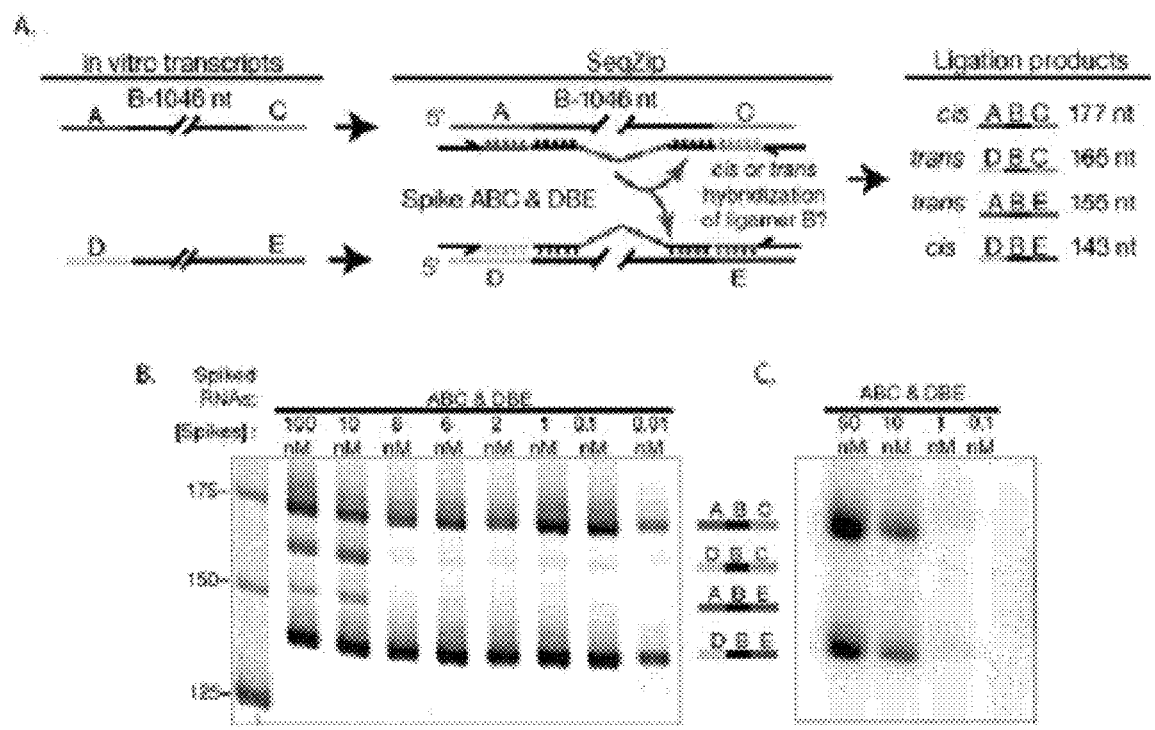
FIG. 18 presents exemplary data investigating trans-transcript hybridization and ligation.

To investigate trans-transcript hybridization experimentally, pairs of in vitro transcribed RNAs were spiked into PolyA selected RNA across a range of concentrations. A ligamer set was designed to test for trans-transcript hybridization over a 1,043 base pair (bp) template loop. See, FIG. 18. (FIG. 3). At concentrations of an RNA spike below 10 nM, the production of trans-ligation events was barely detectable by endpoint PCR (40 cycles). See, FIG. 18B. (FIG. 3, panel B). At concentrations of an RNA spike up to 50 nM, trans-transcript events was barely detectable as compared to cis-ligation events when using semi-quantitative PCR. See, FIG. 18C. (FIG. 3, panel C). The present data show that the vast majority of RNA transcripts (~95%) are expressed across many orders of magnitude below 10 nM when using human tissue RNA-Seq data as a guideline. Wang et al., "Alternative isoform regulation in human tissue transcriptomes" *Nature* 456:470-476 (2008). Although it is not necessary to understand the mechanism of an invention, it is believed that trans-transcript hybridization and ligation is not a confounding technical problem in SeqZip analysis.

D. RNA Extraction For JSL1 Cells

The data presented herein demonstrates identifying exon connectivity based upon one embodiment of the present invention. See, FIG. 5. For example, one method using four different poly(A) selected RNA samples from JSL1 cells. See, FIG. 6. Sample 1 is a 2 week old sample stored at −20° C., samples 2-4 are fresh isolations. Included in the ligamer set was an "R0" control ligamer, allowing for separation of R0 and any potential non-templated ligation events. 'B,' or blank, refers to water added to poly(A) beads in place of an RNA sample. '*' in ligamer addition matrix refers to a set lacking the R0 control ligamer. The data show that: i) the AS isoform expression patterns determined by the present invention are very similar to that of 'resting' JSL1 cells observed using RT-PCR; and ii) no FLLPs were observed for B or '*' samples. Potential PCR artifacts and NTL events were significantly reduced using a second round of poly(A) selection (pre-selection sample data not shown).

E. Mouse Fibronectin Alternative Splicing

In mouse fibronectin, inclusion of the alternatively spliced Extra Domain A (EDA or EDI) exon is believed to promote the inclusion of one of three alternative 3' Splice Sites (3'SS) of the IIICS exon into the same AS. This phenomenon results in a more frequent production of shorter transcripts. See, FIG. 3A.

Fibronectin exon coordination has been reported to occur over six constitutively expressed exons and 800 nt of sequence (5400 nt if introns are considered). Mouse fibronectin (Fn1) is believed to comprise three distinct regions of AS. White et al., "New insights into form and function of fibronectin splice variants" The Journal of Pathology 216:1-14 (2008). The first of these regions comprises the cassette EDA exon. The second region is referred to as the IIICS or V-region exon, and utilizes three different 3' splice sites. Therefore, when these two regions interact, six possible alternatively spliced isoforms may be produced. Fn1 isoforms may be annotated according to the presence or absence of the EDA exon (+ or −) followed by a reference to a IIICS exon 3' splice site (i.e., for example, 120, 95, or 0). The annotation for the IIICS refers to the number of extra amino acids encoded by the differential use of splice sites. The EDA and IIICS exons are believed to be separated by almost 6 kb of genomic sequence and transcribe approximately 815 nt of mRNA including at least six (6) constitutive exons.

Conventional RT-PCR methods that might establish connectivity between these two exons require analysis of cDNAs ranging in size from 1 to 1.6 kb. In one embodiment, the SeqZip method may be performed using cDNAs ranging length between approximately 125-275 nt. Although it is not necessary to understand the mechanism of an invention, it is believed that this >5 fold reduction in sequence length greatly simplifies Fn1 isoform analysis of connectivity and abundance by using embodiments employing a SeqZip method.

Figure 5:
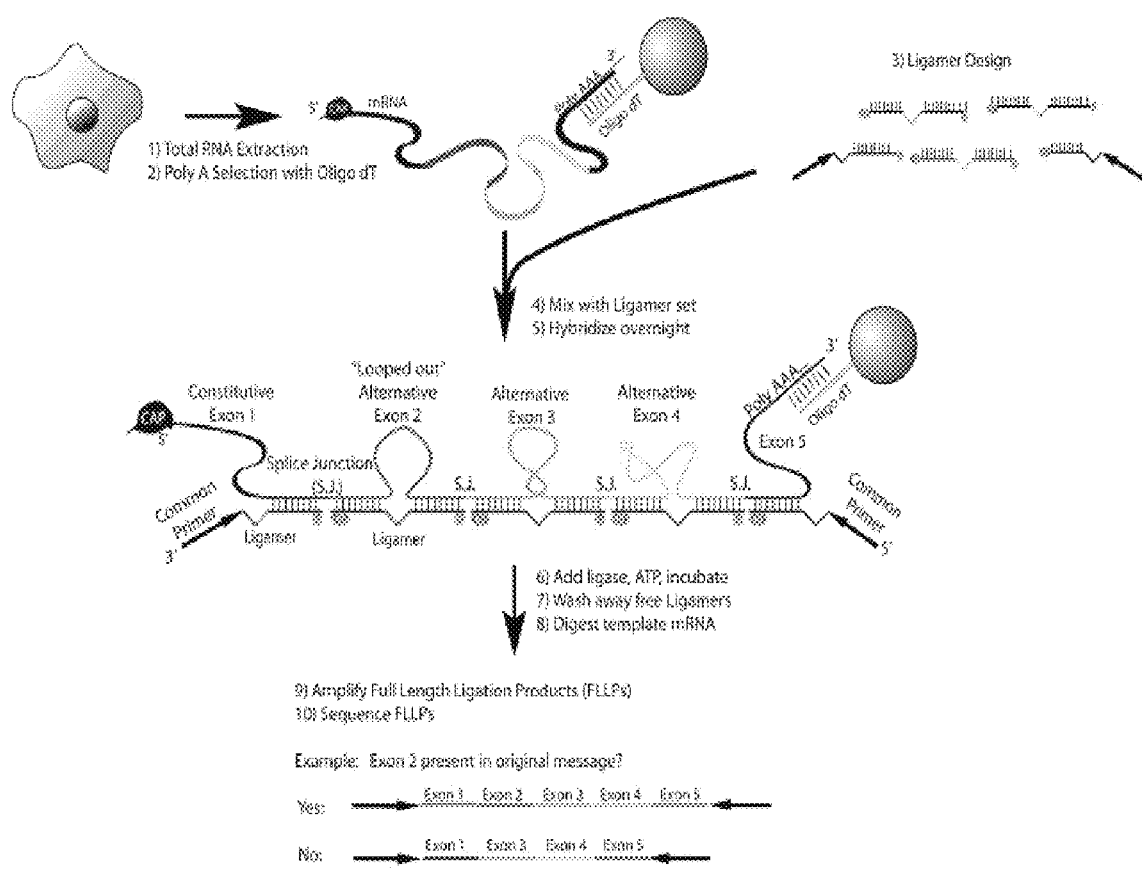
FIG. 5 presents one embodiment of a method comprising a looping out of intervening mRNA sequence wherein exon connectivity is maintained.
Figure 19:
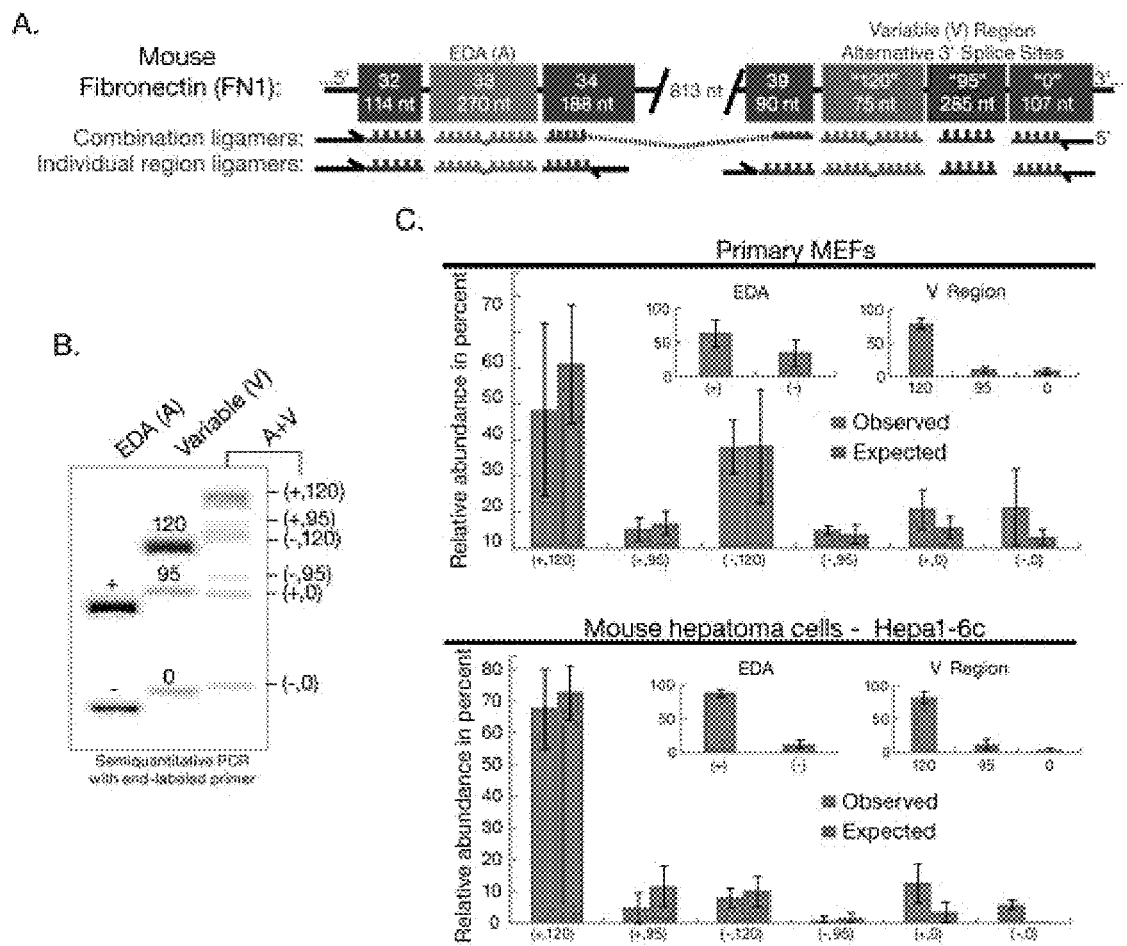
FIG. 19 presents exemplary data showing that SeqZip maintains connectivity between distant Fn1 exons.

Previous reports have suggested that inclusion of the EDA exon promotes splicing from the "0" 3' splice site of the IIICS exon. Fededa et al., "A polar mechanism coordinates different regions of alternative splicing within a single gene" Molecular Cell 19:393-404 (2005); and Chauhan et al., "Alternative splicing of fibronectin: a mouse model demonstrates the identity of in vitro and in vivo systems and the processing autonomy of regulated exons in adult mice" Gene 324:55-63 (2004). This hypothesis was tested using wild type primary mouse embryonic fibroblast (MEF) cells, wherein inclusion frequencies were obtained for the EDA and IIICS exons, alone, and in combination. See, FIG. 19B. (FIG. 5, panel B). If the data shows a deviation between expected and observed Fn1 isoform distribution, then this hypothesis of coordination between splicing decisions in cis between these two exons would be confirmed. However, in contrast to these previous reports, the present data showed no deviations between expected and observed isoform distribution, therefore suggesting that independent splicing decisions are occurring with respect to these two loci.

Figure 6:
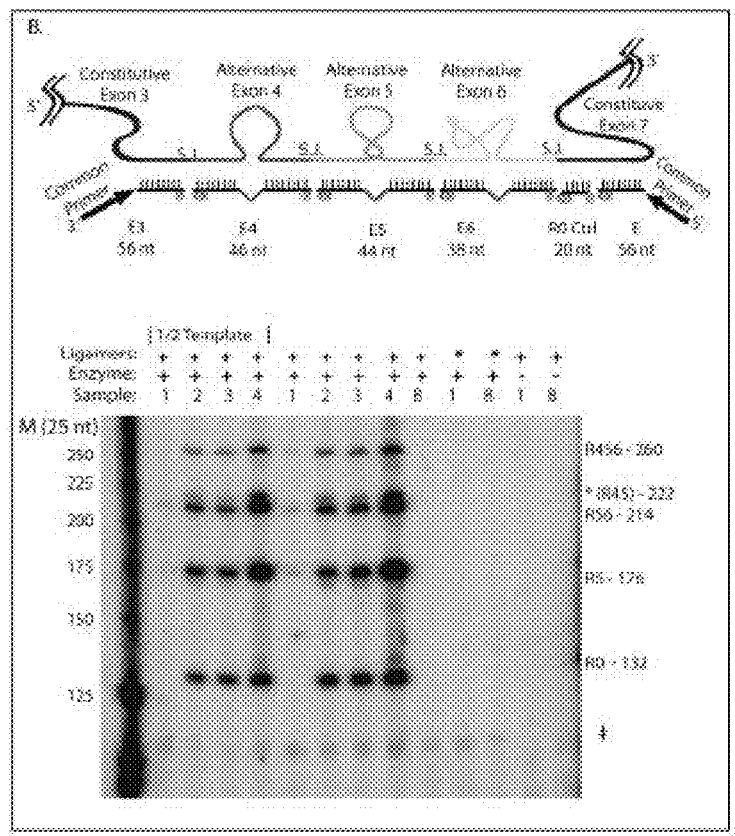
FIG. 6 presents exemplary exon connectivity data from mRNA samples of JSL1 cells. Band marked as ‡ is not observed in lanes lacking enzyme.
Figure 20:
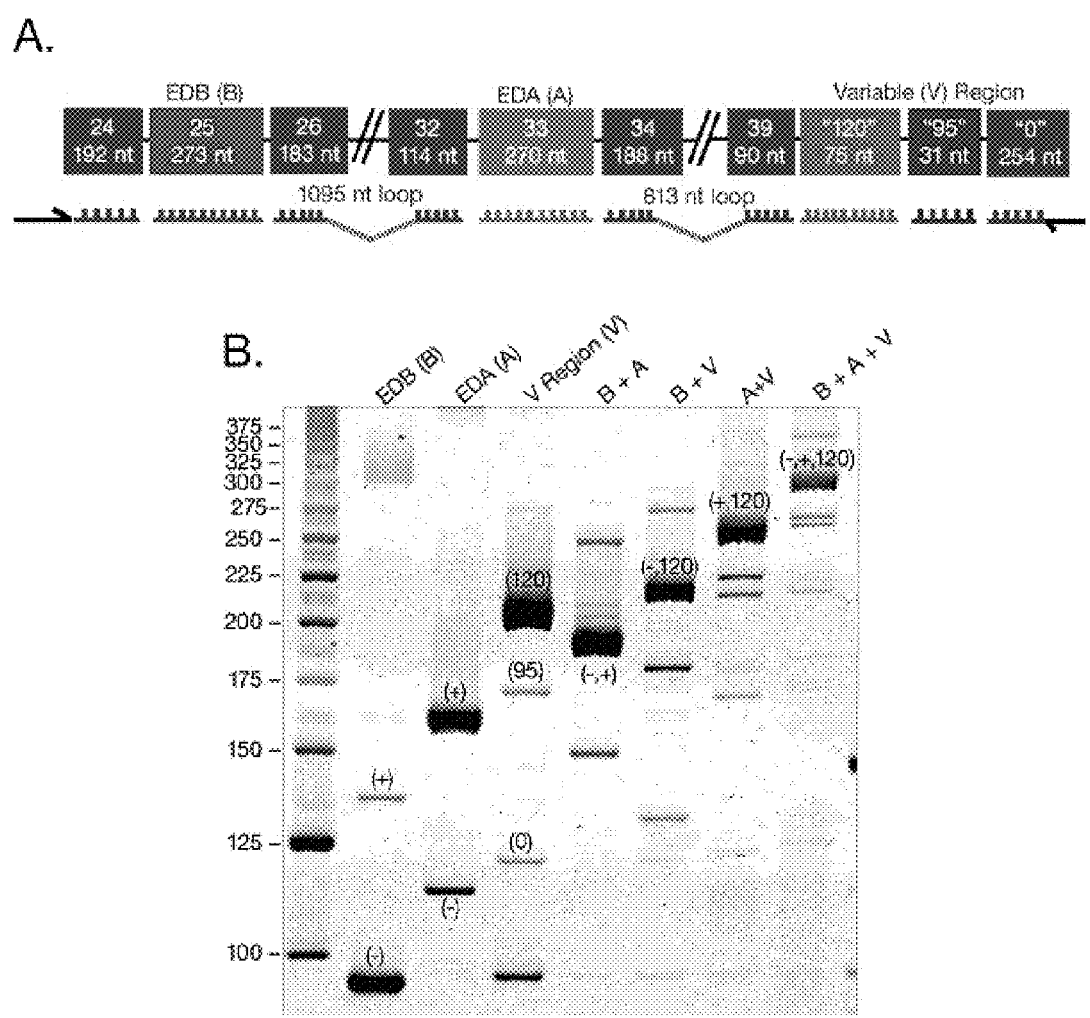
FIG. 20 presents exemplary data using all alternative exons of the Fn1 gene demonstrating that SeqZip simplifies complex alternative splicing.

A third Fn1 cassette exon called EDB or EDII was also studied. See, FIG. 20A. (FIG. 6, panel A). When considering EDB's possible interactions with EDA and/or IIICS, there are twelve possible isoforms of mouse Fn1. In one embodiment, the SeqZip method profiled all twelve isoforms in a single ligation reaction. The data presented herein demonstrates that all twelve isoforms of mouse Fn1 were detectable after 35 cycles of PCR. See, FIG. 20B. FIG. 6, panel B with all the caveats of analysis (supra), and after this many cycles of PCR, the apparent relative abundances at each site agree when each site is measured in combination, demonstrating the ability of SeqZip to analyze multiple sites of AS simultaneously.

To examine exon coordination between these AS gene regions, minigene constructs encoding the fibronectin gene exons were constructed that compares wild-type (wt) EDI exons versus modified (Δ) EDI exons. A first construct comprising two wild-type EDI exons (denoted proximal and distal, respectively. pFN-pEDI$^{WT}$/dEDI$^{WT}$) show proximal and distal EDI AS variant-to-promoter ratios of, 0.78±0.04 and 0.24±0.02, respectively. A second construct modified the proximal EDA exon (ΔESE), wherein expression of the proximal EDI AS variant-to-promoter ratio was reduced to zero, and the distal EDI AS variant-to-promoter ratio was reduced by almost 8 fold (0.24 vs 0.03). A third construct modified the distal EDA exon (ΔESE), wherein the proximal EDI AS variant-to-promoter ratio was unaffected (0.78 vs 0.64) while the distal EDI AS variant-to-promoter ratio was again reduced by almost 8 fold ((0.24 vs 0.03). Fededa et al., "A polar mechanism coordinates different regions of alternative splicing within a single gene" Molecular Cell 19:393-404 (2005); and FIG. 3B. These data show that the presence of the proximal EDI facilitated distal EDI AS events, but the distal EDI had no effect on proximal EDI AS events. Additional modifications can be made to the EDI exons to rigorously demonstrate this 'polar coordination' in the EDI minigene constructs (data not shown).

Figure 13:
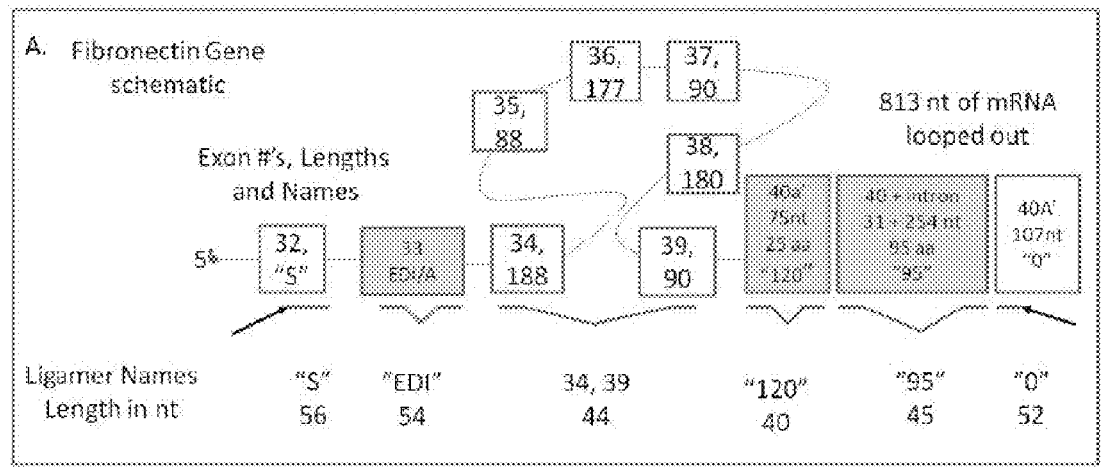
FIG. 13 presents representative ligamer designs capable of observing coordination of AS in mouse fibronectin
Figure 14:
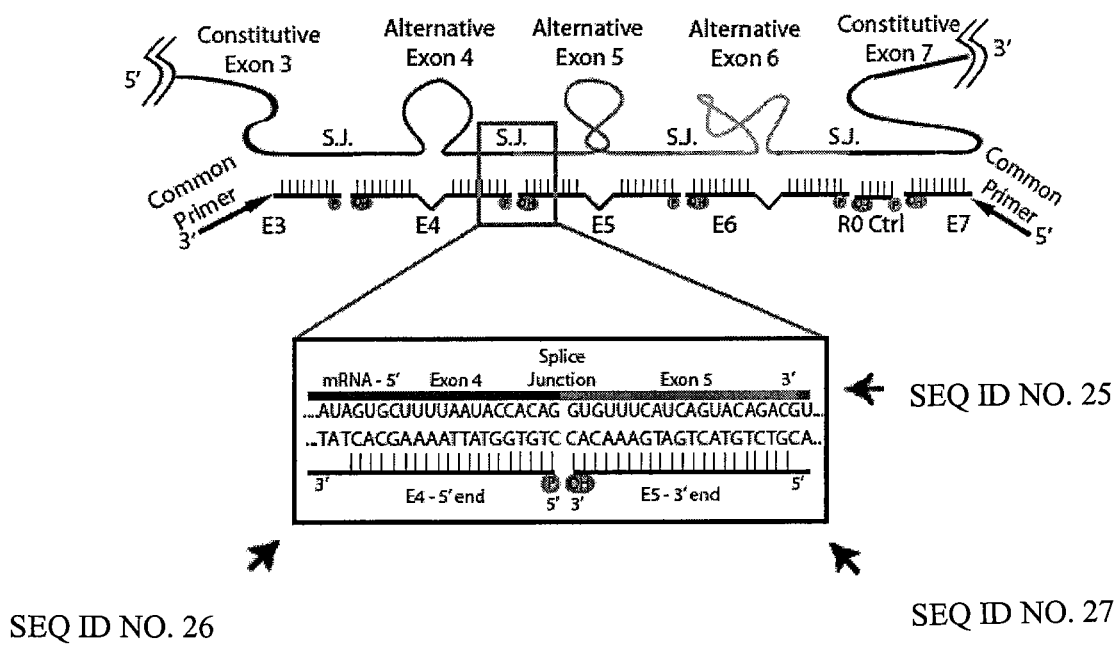
FIG. 14 shows a sequence specific view of ligamers targeting exons of the CD45 gene.

Further studies were performed in an EDA knock-out mouse model, where two different mouse strains (EDA$^{-/-}$ and EDA$^{+/+}$) were used. The EDA$^{-/-}$ mouse strain is missing both EDI exon alleles. The EDA mouse strain constitutively express both EDI exons alleles. The data show a >5 fold positive effect on IIICS '0' isoform production in response to EDI exon. See, FIG. 3C. Furthermore, these two strains were bred to create a EDA heterozygous strain (EDA$^{+/-}$). The heterozygote data appears to confirm that EDA exon inclusion promotes IIICS '0' inclusion. For example, the absence of an EDA exon may promote production of fibronectin AS variants that are either 120 amino acids or 95 amino acids in length. See, FIG. 3D. Further, the use of allele specific RT-PCR on heterozygous mice with a constitutively expressed EDI exon suggests that this coordination may occurs in a cis configuration. FIG. 13 demonstrates how one embodiment of the present invention may be used to maintain exon connectivity information for AS isoforms of mouse fibronectin.

F. Human CD45 Alternative Splicing

In one embodiment, the present method was used to detect endogenous AS isoforms of human CD45. A specific set of ligamers targeting CD45 were designed and synthesized. In order to detect endogenous AS isoforms, it was determined that the nucleotide distances to separate the ligamer regions of complementarity should range between approximately 17 and 22 nt. Previous attempts using ligamers having nucleotide distances of approximately 11 and 15 nt between complementary regions were able to detect in vitro AS transcripts in the absence of background RNA. Although it is not necessary to understand the mechanism of an invention, it is believed that improved specificity may be afforded by longer nucleotide sequences between ligamer regions of complementarity thereby overcoming competing hybridization sites in a more complex sample.

Figure 11:
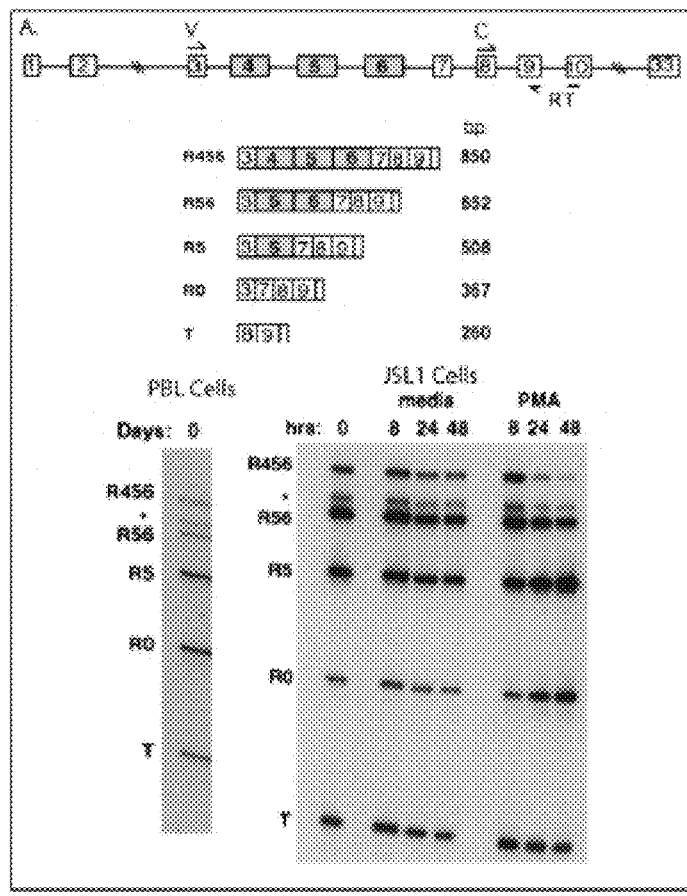
FIG. 11 presents exemplary data showing detection of endogenous isoforms of the human CD45 gene using RT-PCR.

In brief, total RNA was isolated using Tri-reagent. Total RNA was then enriched for poly(A) containing RNA using cellulose beads coated with oligo-dT. Poly(A)-containing RNAs were left on the beads, and a set of ligamers was allowed to hybridize overnight in 1×RNL2 buffer. After overnight hybridization, RNL2 and ATP were added and the samples were incubated for an additional 8 hours. After incubation, unreacted ligamers were washed away, and ligation products were eluted from the beads using RNase digestion at elevated temperature. Full ligation products were selected for, and amplified with, common primers labeled at the 5' end for a limiting number of PCR cycles. Cycle numbers in the linear range of amplification were chosen and confirmed using different template loads. PCR reactions were separated using denaturing PAGE. The results of this experiment correlate well with reported CD45 isoforms as observed using RT-PCR. See, FIG. 11; and Lynch et al., "A Model System for Activation-Induced Alternative Splicing of CD45 Pre-mRNA in T Cells Implicates Protein Kinase C and Ras" *Mol Cell Biol* 20:70-80 (2000). The RT-PCR data employed a set of primers shown at the top of FIG. 11. PCR products from the end-labeled RT and V primers correspond to different isoforms of CD45, with corresponding lengths in nt indicated. By testing peripheral blood leukocytes (PBLs) for CD45 isoform expression pattern, they observed more abundance of R0 and R6 messages. Further, it is believed that the method identified the R45 isoform indicated by the '*'. In contrast, JSL1 cells, having been FACS selected for CD45 protein from the largest isoform, show a markedly highly production of R456 and R56 isoforms. This expression pattern could be changed by treatment with PMA. Cloning and sequencing confirmed the presence of expected ligation products. Additionally, these results suggest that washing the samples after ligation, followed by a limiting number of PCR cycles, limits the observation of most side products.

Consequently, the above data demonstrate that unique mRNAs can serve as templates directing the ligation of ligamers designed to compress sequence content into short, DNA-based products capable of detecting and/or identifying AS isoforms.

G. Multiple Gene Connectivity Analysis

In one embodiment, the present invention contemplates a method for determining exon connectivity by simultaneously profiling multiple genes. In one embodiment, the method identifies intergene exon connectivity and/or coordination. In one embodiment, SeqZip ligation products are analyzed using a high-throughput sequencing approach. In some embodiments, SeqZip can be used for genome-wide analysis of sequence connectivity for mRNA, non-coding RNAs, splicing within introns, novel 'linked' alternative promoter choices, and many other previous uninvestigated questions of RNA biology.

Figure 7:
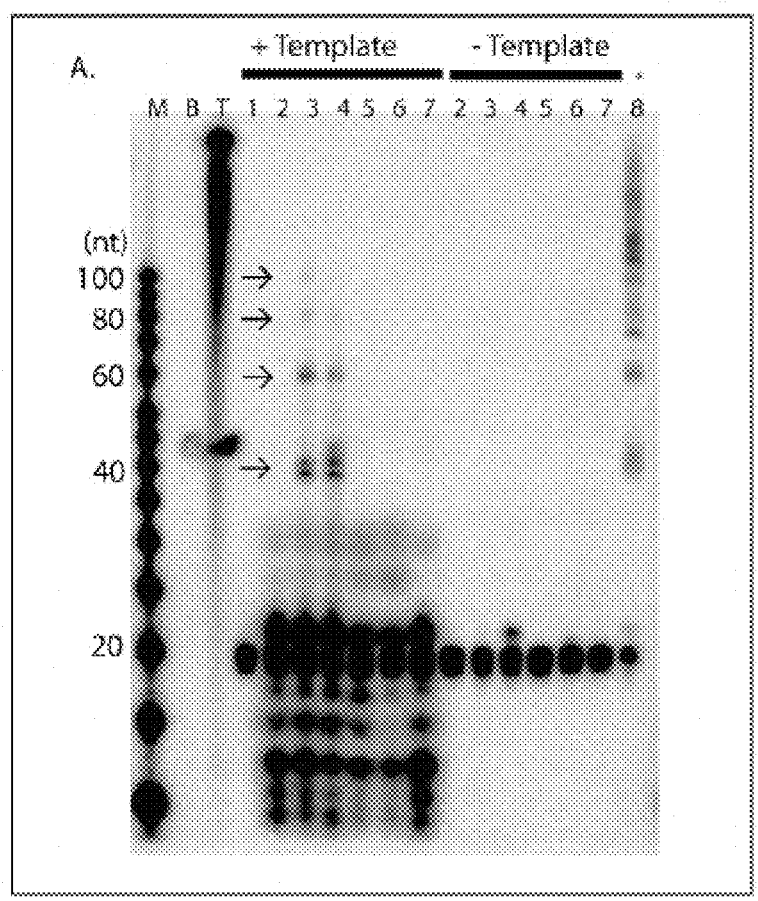
FIG. 7 presents exemplary data showing the ligation efficiency of representative ligases in connecting multiple oligonucleotides using a $^{32}$P-labeled 20 nt ligamers to form a ligated oligonucleotide (shown at bottom).
Figure 7:
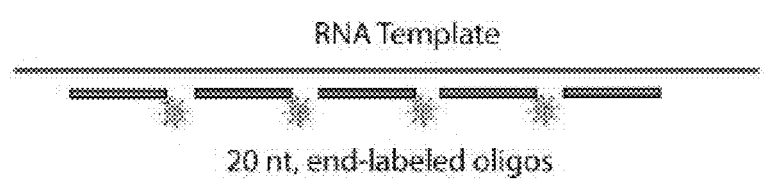
Figures 21A, 21B:
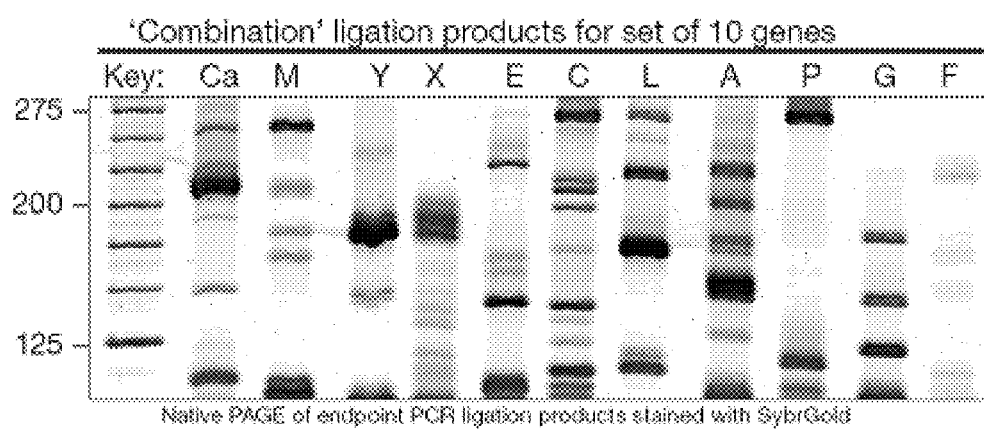
FIG. 21A: Genes and pairs of exons within those genes that may display exon connectivity and/or coordination selected for development of high-throughput analysis of SeqZip ligation products.
FIG. 21B: Gel electrophoresis of SeqZip ligation products maintaining exon connectivity between the exons described in FIG. 21A. The electrophoretic gel analysis shows that SeqZip produces a diverse set of combination products, analysis of which would be difficult without a high-throughput sequencing approach.

The data presented herein examines profiled pairs of exons in a set of ten (10) genes where alternative splicing exon connectivity had been previously suggested. Fagnani et al., "Functional coordination of alternative splicing in the mammalian central nervous system" *Genome Biology* 8:R108-R108 (2007). These ten (10) genes displayed a range of mRNA lengths between the queried exons, from between approximately ~400 to ~4,600 nts. See, FIG. 21A. Examination of splicing decisions involving these exons while maintaining connectivity utilizing current sequencing technologies (i.e., for example, RT-PCR) would be very expensive, labor intensive, and technically problematic. However, some embodiments of the present invention create short ligation products that can be analyzed with current, widely implemented and available high-throughput sequencing platforms. See, FIG. 21B.

mRNA was extracted from C57BL/6J mice and ligation products were created to examine splicing decisions at each exon independently, and in combination. Ligation products were then analyzed using a paired-end read sequencing strategy on the Illumina GE2 platform. See, FIG. 22A. (FIG. 7, panel A).

Figure 22:
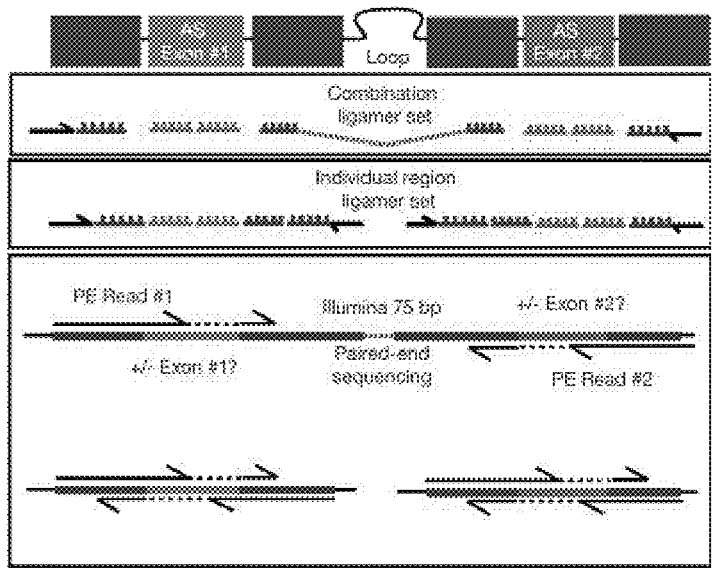
FIG. 22 presents exemplary data demonstrating that SeqZip is adaptable multiple gene analysis and high-throughput analysis
Figure 22:
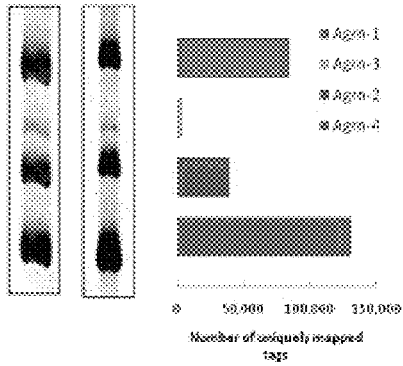

SeqZip ligation products templated by mRNAs transcribed from the mouse AGRN gene are similar to those observed using conventional RT methods in regards to the number of observed isoforms and their relative abundance. See, FIG. 22B (SeqZip). FIG. 7, panel B, 'SeqZip'. Further, when high-throughput sequencing (HTS) tag mapping to isoform-specific AGRN ligation products was quantified, the relative tag count is also similar to those observed on traditional gel electrophoresis analysis. FIG. 22B. Although it is not necessary to understand the mechanism of an invention, it is believed that this data demonstrates the utility of using HTS in the analysis of SeqZip ligation products. Many other isoforms from the other nine (9) genes examined were also detected in this library, demonstrating multiplex analysis is also possible (data not shown).

IV. Quantitative Exon Connectivity Bias Analysis

Biases affecting accurate quantitation may be introduced by the efficiency of ligation and amplification when using PCR. Generally, as the number of ligation events increase in order to detect larger products, a natural bias is introduced towards detecting smaller products with fewer ligations. For example, consider the situation where two isoforms of a transcript exist in the same sample. One isoform has two 'extra' exons compared to the other. The isoform with the extra exons is twice as abundant compared to the shorter isoform. A potential source of bias with respect to measuring relative isoform abundances is that the longer isoform requires two more ligation events per template in order to be detected. As ligation events are not efficient, we may observe more ligation product resulting from the shorter isoform simply because it requires less ligation events, regardless of its lower abundance compared to the longer isoform.

Nonetheless, an exon connectivity assay may still detect a greater abundance of shorter isoforms containing fewer exons, simply because fewer ligation events occur. One model to test this potential problem involves the continued examination of the human CD45 gene using the JSL1 cell line.

The immortalized human Jurkat cell line exhibits many features associated with constitutive T-cell activation (i.e., for example, the surface receptor protein CD45 expression profile). As such, Jurkat cells predominately express CD45 protein products derived from the smallest isoform, R0. However, it has been noted that 'activated' T-cells will spontaneously switch back to high expression of larger CD45 isoforms. Rothstein et al., "Cyclic regulation of CD45 isoform expression in a long term human CD4+CD45RA+ T cell line" *Journal of Immunology* 146:1175-1183 (1991). Taking advantage of this phenomenon, a limiting dilution method followed by flow cytometry may obtain monoclonal lines expressing the largest isoforms of CD45. Lynch et al., "A Model System for Activation-Induced Alternative Splicing of CD45 Pre-mRNA in T Cells Implicates Protein Kinase C and Ras" *Mol Cell Biol* 20:70-80 (2000). One particular line, called Jurkat Splicing Line 1 (JSL1) also responds to treatment with phorbol 12-myristate 13-acetate (PMA), a diacylglycerol mimic that activates protein kinase C (PKC), resulting in a signaling cascade similar to that of T-cell activation. This activation changes the CD45 isoform expression back to the smaller isoforms. Through examination of isoforms of CD45 in 'resting' and 'activated' JSL1 cells, the number of ligations per isoform introduces a bias towards detection of isoforms requiring fewer ligation events.

PCR represents another major potential source of bias. Although both microarray and RNA-Seq (HTS) analysis usually involve a PCR amplification step, input samples are typically sheared such that every template is very similar in size and presumably equally amplified (i.e., for example, homogenous in size and frequency). PAGE analysis usually involves multiplex amplification of different length templates. Therefore, quantitative accuracy needs to account for the possibility of PCR selectively amplifying shorter products and skewing the reported relative abundances. Accordingly, limiting the number of PCR cycles may maintain amplification in the linear range. The results are verified by comparison to a quantitative RT-PCR (qRT-PCR) study using CD45 isoform-specific primers that is not subject to small size bias.

The above data demonstrates that multiple ligamer exon connectivity accurately identifies endogenous CD45 isoforms. See, FIG. 11. These data suggest that a higher abundance of the R456 isoform relative to the R0 isoform in untreated JSL1 cells would be expected, and that the number of ligation events would be not a major source of bias. Sensitivity and quantitative ability to detect changes in relative CD45 isoform abundance can be tested by using the JSL1 cell line before and after PMA treatment. It is expected that the observed relative expression of each AS isoform agrees with published and input qRT-PCR data, thereby suggesting that there is little or no bias imparted by the number of ligation events or introduced in any other steps of our technique.

Figure 12A:
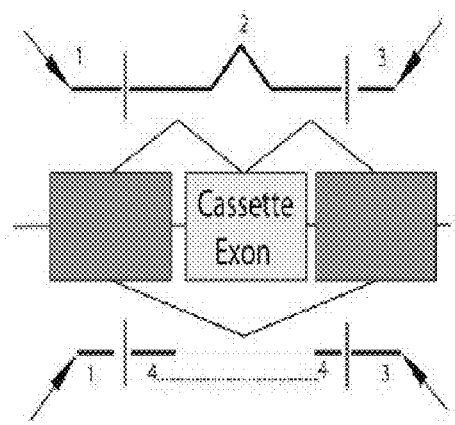
FIG. 12 presents several embodiments of an alternative multiple ligamer exon connectivity configuration.
Figure 12B:
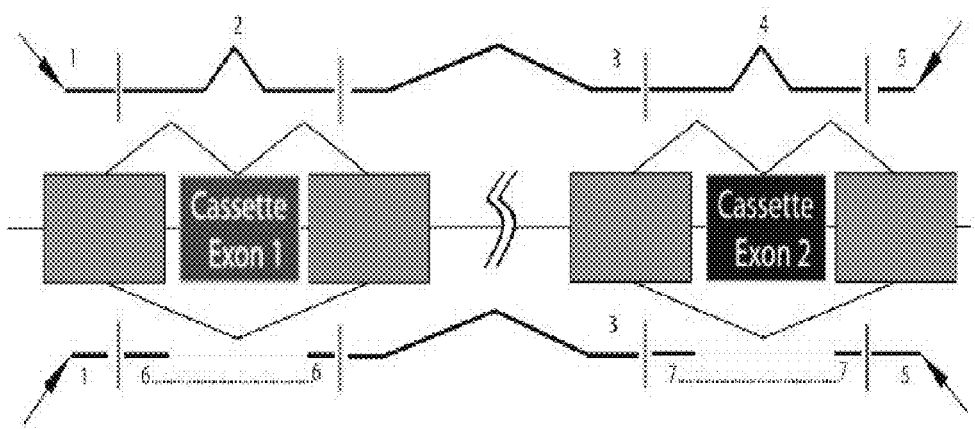

In one embodiment, the present invention contemplates a method for identifying inter-gene splicing variants. In one embodiment, an alternative splice variant comprises a first exon from a first gene and a second exon from a second gene. In one embodiment, the present invention contemplates a method for identifying inter-chromosomal splicing variants. In one embodiment, an alternative splice variant comprises a first exon from a first chromosome and a second exon from a second chromosome. Although it is not necessary to understand the mechanism of an invention, it is believed that such inter-gene and inter-chromosomal splicing variants may be facilitated by tertiary and/or quaternary folding of either the chromosome or chromatin/nuclear structure. In one embodiment, the present invention contemplates a method comprising an alternative multiple ligamer design scheme. See, FIG. 12. In one embodiment, the ligations are placed within exons, instead of at splice junctions. For example, the alternative ligamer design comprises a single cassette exon event. See, FIG. 12A. As shown, Primers 1 and 3 hybridize to the two green, constitutive exons, approximately 8-11 nt from the splice junction bordering the yellow cassette exon. Ligamer 2 has two regions of complementarity that span the splice junction and capture a looped conformation of the cassette exon. If all ligamers hybridize to the transcript, two ligation events (red lines) will join them together, allowing PCR amplification using the sequences incorporated in ligamers 1 and 3. If the cassette exon is not present, then ligamer 4 will preferentially hybridize across the splice junction, resulting in 16-22 nt of combined complementarity to the message. Although it is not necessary to understand the mechanism of an invention, it is believed that this method allows for sufficient specificity at the selected hybridization temperature condition of the experiment to detect the absence of the alternatively spliced exon. Further, a two-cassette exon event is also demonstrated. See, FIG. 12B.

It should be noted that the alternative multiple ligamer design embodiment each ligamer spans a queried splice junction. Although it is not necessary to understand the mechanism of an invention, it is believed that this method will normalize the number of required ligation events between two isoforms of different sequence composition. It is further believed that a greater number of ligamers may be used as compared to the design scheme where ligation events occur at splice junctions For example, for analysis of a one cassette exon event, a simple ligamer design scheme may utilize three ligamers, whereas an alternative approach may utilize four ligamers. Similarly, if a transcript comprises two cassette exon events, an alternative design scheme may use seven ligamers instead of five.

III. RNA Detection Methodologies

A. High-Throughput Sequencing

High-Throughput Sequencing (HTS) devices are compatible with a variety of sequencers for reading ligamer barcodes in an efficient and cost effective manner (i.e., for example, SOLiD® Sequencer, Applied Biosystem's).

The high demand for low-cost sequencing has driven the development of high-throughput sequencing technologies that parallelize the sequencing process, producing thousands or millions of sequences at once. Hall N, "Advanced sequencing technologies and their wider impact in microbiology" *J. Exp. Biol.* 210: 1518-1525 (2007); and Church G. M. "Genomes for all" *Sci. Am.* 294: 46-54 (2006). High-throughput sequencing technologies are intended to lower the cost of DNA sequencing beyond what is possible with standard dye-terminator methods.

1. In Vitro Clonal Amplification

Molecular detection methods are not sensitive enough for single molecule sequencing, so most approaches use an in vitro cloning step to amplify individual DNA molecules. Emulsion PCR isolates individual DNA molecules along with primer-coated beads in aqueous droplets within an oil phase. Polymerase chain reaction (PCR) then coats each bead with clonal copies of the DNA molecule followed by immobilization for later sequencing. Emulsion PCR has been commercialized by: i) 454 Life Sciences. Margulies et al., "Genome sequencing in microfabricated high-density picoliter reactors" *Nature* 437: 376-380 (2005); ii) polony sequencing, Shendure et al, (September 2005). "Accurate multiplex polony sequencing of an evolved bacterial genome". Science 309 (5741): 1728-32 (2005); and iii) SOLiD sequencing, (developed by Agencourt, now Applied Biosystems). Another method for in vitro clonal amplification is bridge PCR, where fragments are amplified upon primers attached to a solid surface. The single-molecule method was commercialized by Helicos and skips the amplification step, directly fixing DNA molecules to a surface. Braslaysky et al., "Sequence information can be obtained from single DNA molecules" *Proc. Natl. Acad. Sci. U.S.A.* 100: 3960-3964 (2003).

2. Parallelized Sequencing

In this method, DNA molecules are physically bound to a surface, and sequenced in parallel. Sequencing by synthesis, like dye-termination electrophoretic sequencing, uses a DNA polymerase to determine the base sequence. Reversible terminator methods (used by Illumina and Helicos) use reversible versions of dye-terminators, adding one nucleotide at a time, detect fluorescence at each position in real time, by repeated removal of the blocking group to allow polymerization of another nucleotide. Pyrosequencing (used by 454) also uses DNA polymerization, adding one nucleotide species at a time and detecting and quantifying the number of nucleotides added to a given location through the light emitted by the release of attached pyrophosphates. Ronaghi et al., "Real-time DNA sequencing using detection of pyrophosphate release" *Analytical Biochemistry* 242: 84-9 (1996).

3. Ligation Sequencing

This enzymatic sequencing method uses a DNA ligase to determine the target sequence. Macevicz S. C., "DNA sequencing by parallel oligonucleotide extensions" U.S. Pat. No. 5,750,341 (herein incorporated by reference). Used in the polony method and in the SOLiD technology, it uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

4. Microfluidic Sanger Sequencing

In microfluidic Sanger sequencing the entire thermocycling amplification of DNA fragments as well as their separation by electrophoresis is done on a single chip (approximately 100 cm in diameter) thus reducing the reagent usage as well as cost. In some instances, the use of microchips can increase the throughput of conventional sequencing. Research will still need to be done in order to make this use of technology effective.

5. Hybridization Sequencing

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identifies its sequence in the DNA being sequenced. Hanna et al., "Comparison of sequencing by hybridization and cycle sequencing for genotyping of human immunodeficiency virus type 1 reverse transcriptase". *J. Clin. Microbiol.* 38: 2715-2721 (2000). Mass spectrometry may be used to determine mass differences between DNA fragments produced in chain-termination reactions. Edwards et al., "Mass-spectrometry DNA sequencing" *Mutation Research* 573: 3-12 (2005).

B. Northern Blot—Hybridization mRNA expression may be measured by any suitable method, including but not limited to, those disclosed below. In some embodiments, RNA is detection by Northern blot analysis. Northern blot analysis involves the separation of RNA and hybridization of a complementary labeled probe.

In other embodiments, RNA (or corresponding cDNA) is detected by hybridization to a oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe comprising an oligonucleotide with a 5'-reporter dye (e.g., a fluorescent dye) and a 3'-quencher dye may be included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR(RT-PCR) may be used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

C. Enzymatic Cleavage—Hybridization

In other embodiments, RNA expression is detected by enzymatic cleavage of specific structures (INVADER assay, Third Wave Technologies; See e.g., U.S. Pat. Nos. 5,846,717, 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

D. Remote Detection Systems

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, wherein the information is provided to medical personal and/or subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor. In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

IV. Kits

In another embodiment, the present invention contemplates kits for the practice of the methods of this invention. The kit can optionally include a plurality of ligamers, wherein each of said ligamers comprise a single different barcode sequence and a plurality of different complementarity regions. The kit can optionally include a template oligonucleotide, wherein said oligonucleotide comprises a plurality of hybridization sites. The kit can optionally include buffers and reagents for hybridizing said ligamers and template oligonucleotide. The kit can optionally include a ligase and associated buffers and reagents. The kit can optionally include enzymes capable of performing PCR (i.e., for example, DNA polymerase, Taq polymerase and/or restriction enzymes). The kits may also optionally include appropriate systems (e.g. opaque containers) or stabilizers (e.g. antioxidants) to prevent degradation of the reagents by light or other adverse conditions.

The kits may optionally include instructional materials containing directions (i.e., protocols) providing for the use of the reagents in, for example, hybridizing said ligamers and said template oligonucleotide; and/or ligating said ligamers to create a full length ligated product.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In other embodiments, the present invention provides kits for the detection and characterization of nucleic acids (i.e., for example, mRNA). In some embodiments, the kits contain detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

EXPERIMENTAL

Example I

The Multiple Ligamer Exon Connectivity Assay

This example demonstrates protocol showing how a sequence of the mRNA strand may be captured in a 'looped out' conformation through hybridization to the two complementary ligamer regions. See, FIG. 5.

In general, the method comprising the steps of:
1) Total RNA may be extracted from sample using standard protocols (TriReagent, TriZol, etc).
2) Total RNA is enriched for poly(A) sequences using Oligo dT purification.
3) Ligamers targeted to transcript region of interest are synthesized with appropriate 5' phosphates and common PCR sequences.
4) Pool of ligamers is mixed with transcript at desired concentration.
5) Sample is heated to relax RNA secondary structure, while maintaining poly(A) hybridization (i.e. between 55° C. and 60° C.). This is followed by overnight hybridization at 15° C. below the normalized Tm of ligamers.
6) Ligase is added at desired concentration and allowed to catalyze ligation for desired amount of time.
7) Using the Oligo dT beads as a handle, unreacted ligamers and other side products of the ligation step are washed away.
8) RNA transcripts are degraded using RNase, freeing the Full Length Ligation Products (FLLPs) from the Oligo dT Beads.
9) Using common primer sequences, FLLPs are amplified using a limiting number of PCR cycles.
10) FLLPs are sequenced, revealing exon order and content of original transcript.

Example II

Ligamer Design

The 5' and 3' most sequences of a target sequence (ex. exon or multiple exons) were obtained from online databases (ACEview, UCSC, etc.). The $T_m$ of these sequences was normalized to 60° C.±5° C. according to nearest-neighbor rules (Xia, SantaLucia et al. 1998) by adding or removing target nucleotides. Most sequences fell between 12 and 25 nucleotides of hybridization. After assembling target regions, matching sequences (i.e. the 5' and 3' edge sequences of a specific exon) were combined, and a short linker sequences was included between them (i.e., for example, ACTACT). With the full sequence now assembled, the reverse complement was taken, ligamers requiring 5' phosphorylation for subsequent ligation were marked, and ligamers were ordered in a 96 well format (Integrated DNA Technologies). Ligamers were reconstituted at 1 uM into 'sets' targeting specific areas of compression and subsequently diluted for use in the SeqZip protocol.

Example III

Exon Connectivity Determination Method (e.g., SeqZip)

Total RNA was isolated from cell line or tissue using according to the manufacturer's instructions (TriReagent, MRC Inc.). Poly(A) RNA was isolated using a commercially available kit. (Poly(A)Purist™ MAG, Ambion (AM1922)). Poly(A) RNA was not eluted from magnetic beads, and after the last wash step, beads were aliquoted into appropriate amounts and reconstituted in hybridization buffer (60 mM Tris-HCl pH 7.5 @ 25° C., 1.2 mM DTT 2.4 mM MgCl, 480 uM ATP) including 10 nM of all appropriate ligamers.

Hybridization was performed in a thermocycler by heating samples to 62° C. for 5 minutes and cooling to 45° C. in 3°

C.×10 minute increments. Samples were left at 45° C. for 1 hour, then cooled again in 3° C.×10 minute increments until 37° C. was reached. Samples were left at 37° C. until enzyme was added. T4 RNA ligase 2 (NEB, MO239) was added to compose 10% of final volume (i.e., for example, 5 uL in 45 uL of previous samples). At this point the samples were in 1× ligation buffer (51 mM Tris-HCl pH 7.5 @ 25° C., 2.01 mM DTT, 5 mM KCl, 2 mM MgCl, 400 uM ATP, 3.5 mM (NH4)2SO4, 5% glycerol). Samples were incubated at 37° C. for 12-16 hours. Ligation products amplified by PCR and analyzed accordingly.

Example IV

Reverse Transcriptase Polymerase Chain Reaction (RT-PCR)

Reverse transcription was performed using SuperScript III (Invitrogen) using 200 ng of Poly(A) selected RNA and an anchored oligo-dT primer. cDNAs were used for Q-PCR and endpoint PCR experiments.

Example V

Semi-quantitative PCR Analysis

Antisense PCR primers were end-labeled with γ-ATP. Primers were quantified and used in PCR reactions for a limiting number of cycles. Multiple cycle numbers were performed to test for expected increases in signal (i.e., for example, 15, 18, and/or 21 cycles). Reactions were run out on denaturing acrylamide gels to resolve different sized ligation products. Bands were quantified using a Typhoon imager (GE Healthcare) and the ImageQuant software package (GE Healthcare).

Example VI

RNA Tissue Sample Collection

For brain samples, one hemisphere of mouse brain (including cerebellum) was obtained from a male C57BL/6J. The tissue was homogenized in 20 mL of Tri-reagent and isolated according to manufactures protocol. Total RNA was also obtained from the liver (right lobe) in a similar manner.

Example VII

Deep Seq Workup

Illumina PE library sequence primers were included in flanking ligamer design. After SeqZip performed in accordance with Example III, samples were pre-amplified for 20 cycles with primers matching the Illumina PE adaptor sequences. After PCR samples were PCR purified (Qiagen PCR purification kit), full tempated ligation products were size selected on a 6% polyacylamide gel. Samples were amplified for an additional 10 cycles using Illumina's PE primers #1 and #2. Samples were again PCR purified and unincorporated primers were removed by gel size selection. Libraries were quantified using a Bioanalyzer and analyzed on the GE-II platform (Illumina) using the paired-end 75 nt read workflow.

We claim:

1. A method, comprising:
   a) providing:
      i) a plurality of ligamer subsets, wherein each of said ligamer subsets comprise a plurality of different complementary regions, wherein at least two of said plurality of different complementarity regions are separated by a central region, wherein said central region has a different exon-specific barcode sequence, wherein each said different barcode sequence comprises a different identifier code for a different specific exon, wherein said at least two of said different complementarity regions are complementary to the flanking regions of said different specific exon; and
      ii) a template oligonucleotide, wherein said oligonucleotide comprises a plurality of hybridization sites;
   b) mixing said plurality of ligamers with said template oligonucleotide under conditions such that said complementarity regions bind to said hybridization sites;
   c) ligating said ligamers to create a full length ligated product (FLLP);
   d) amplifying said FLLP under conditions to create a DNA product; and
   e) identifying the consecutive order of said barcodes within said DNA product.

2. The method of claim 1, wherein said template oligonucleotide comprises an mRNA oligonucleotide.

3. The method of claim 2, wherein said mRNA oligonucleotide comprises a plurality of said different exons.

4. The method of claim 1, wherein each of said barcodes corresponds to one of said different exons.

5. The method of claim 1, wherein said identifying comprises nucleotide sequencing.

6. The method of claim 5, wherein said sequencing comprises high throughput sequencing.

7. The method of claim 1, wherein said template oligonucleotide ranges between approximately 100-100,000 nt.

8. The method of claim 1, wherein said ligamer ranges between approximately 5-2,000 nt.

9. The method of claim 1, wherein said DNA product ranges between approximately 100-1000 nt.

10. A kit, comprising:
    a) a first container comprising a plurality of ligamer subsets, wherein each of said ligamer subsets comprise a plurality of different complementarity regions, wherein at least two of said plurality of different complementarity regions are separated by a central region, wherein said central region has a different exon-specific barcode sequence, wherein each different exon-specific barcode sequence comprises a different identifier code for a different specific exon, wherein said at least two of said different complementarity regions are complementary to the flanking regions of said different specific exon; and
    b) a second container comprising a template oligonucleotide, wherein said oligonucleotide comprises a plurality of hybridization sites;
    c) a third container comprising buffers and reagents for hybridizing said ligamers and template oligonucleotide;
    d) a fourth container comprises a ligase and associated buffers and reagents; and,
    e) a set of instructions for;
       i) hybridizing said ligamers and said template oligonucleotide;
       ii) ligating said ligamers to create a full length ligated product.

* * * * *